(12) United States Patent (10) Patent No.: US 6,980,863 B2
van Venrooij et al. (45) Date of Patent: Dec. 27, 2005

(54) NEUROLOGICAL STIMULATION LEAD EXTENSION

(75) Inventors: Paul van Venrooij, Hoensbroek (NL); Victor Duysens, Grevenbicht (NL)

(73) Assignee: Medtronic, Inc., Minneapolis, MN (US)

( * ) Notice: Subject to any disclaimer, the term of this patent is extended or adjusted under 35 U.S.C. 154(b) by 245 days.

(21) Appl. No.: 10/395,321

(22) Filed: Mar. 20, 2003

(65) Prior Publication Data

US 2004/0186542 A1 Sep. 23, 2004

(51) Int. Cl.⁷ .............................. A61N 1/05
(52) U.S. Cl. .................................... 607/116
(58) Field of Search ............... 607/9, 37, 115–117; 439/223, 287, 909, 557, 668, 669

(56) References Cited

U.S. PATENT DOCUMENTS

| | | | |
|---|---|---|---|
| 4,744,371 A * | 5/1988 | Harris | 607/117 |
| 4,850,359 A | 7/1989 | Putz | |
| 5,000,177 A | 3/1991 | Hoffmann et al. | |
| 5,080,096 A | 1/1992 | Hooper et al. | |
| 5,328,442 A | 7/1994 | Levine | |
| 6,233,488 B1 | 5/2001 | Hess | |
| 6,343,233 B1 | 1/2002 | Werner et al. | |
| 6,439,911 B1 * | 8/2002 | Conorich | 439/341 |

2003/0028232 A1 2/2003 Camps et al.

FOREIGN PATENT DOCUMENTS

WO WO 00/64535 11/2000

OTHER PUBLICATIONS

G.J.M. Huiskamp, F.S.S. Leijten, A.C. van Huffelen, MEG Source Localization of Interictal Activity in Temporal Lobe Epilepsy, May 7, 2001.
Notification of Transmittal of the International Search Report and the Written Opinion of the International Searching Authority, or the Declaration for PCT Application PCT/US2004/008591, filed Mar. 18, 2004.

* cited by examiner

*Primary Examiner*—Scott M. Getzow
(74) *Attorney, Agent, or Firm*—Shumaker & Sieffert, P.A.

(57) ABSTRACT

The invention is directed to neurological lead extensions without set screws, set screw blocks, or set screw inserts. Such elimination of set screws, blocks and inserts can reduce the amount of metal and ferromagnetic material in the extension. The neurological lead extension may include a proximal end configured to couple to a neurological device and a distal end configured to couple to an implanted neurological lead. A set of electrical contacts are disposed in proximity to the distal end to provide electrical contact to an inserted end of the implanted neurological lead. Various elements and structures are described which can mechanically secure the inserted end of the implanted neurological lead to the distal end of the extension.

35 Claims, 23 Drawing Sheets

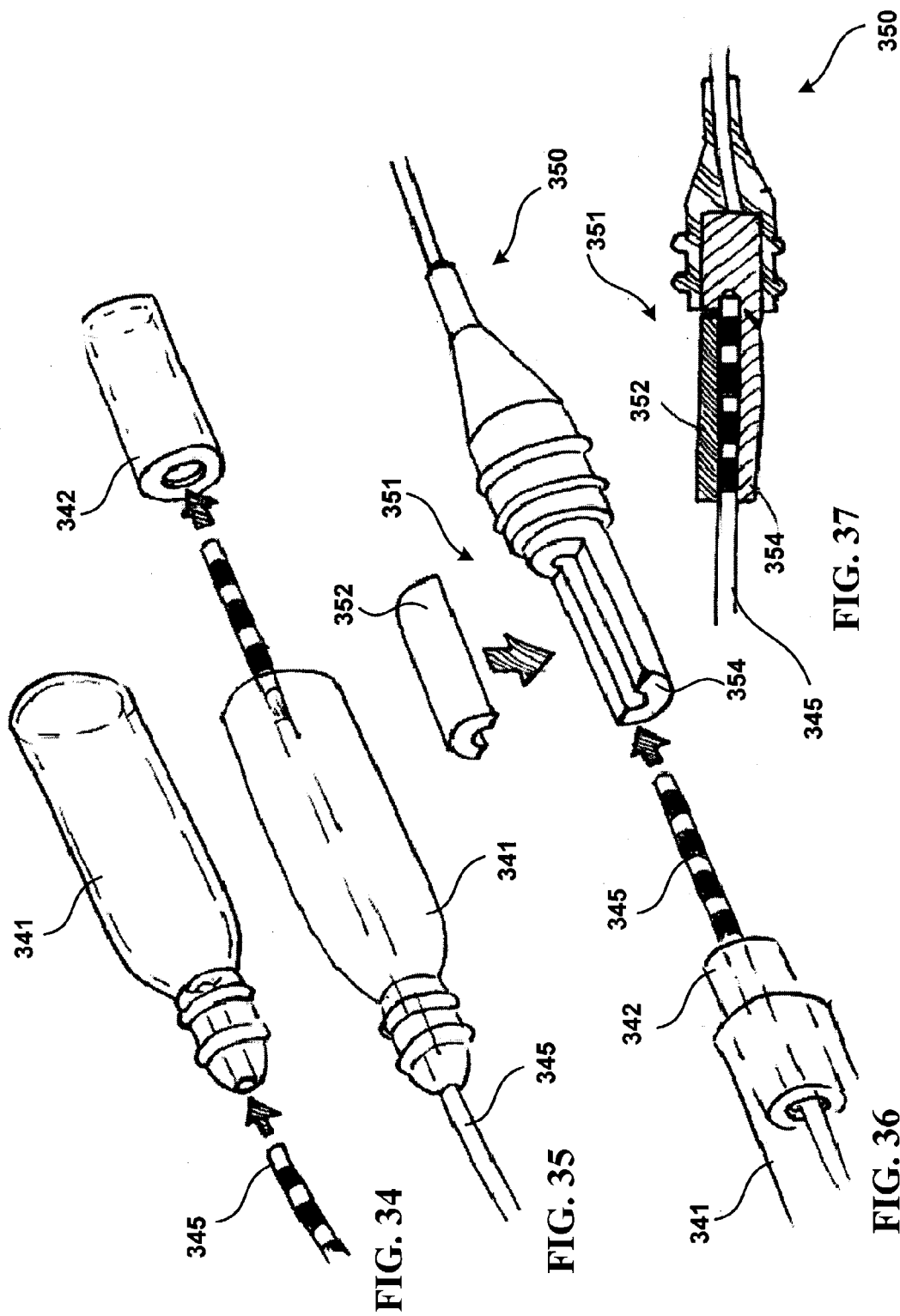

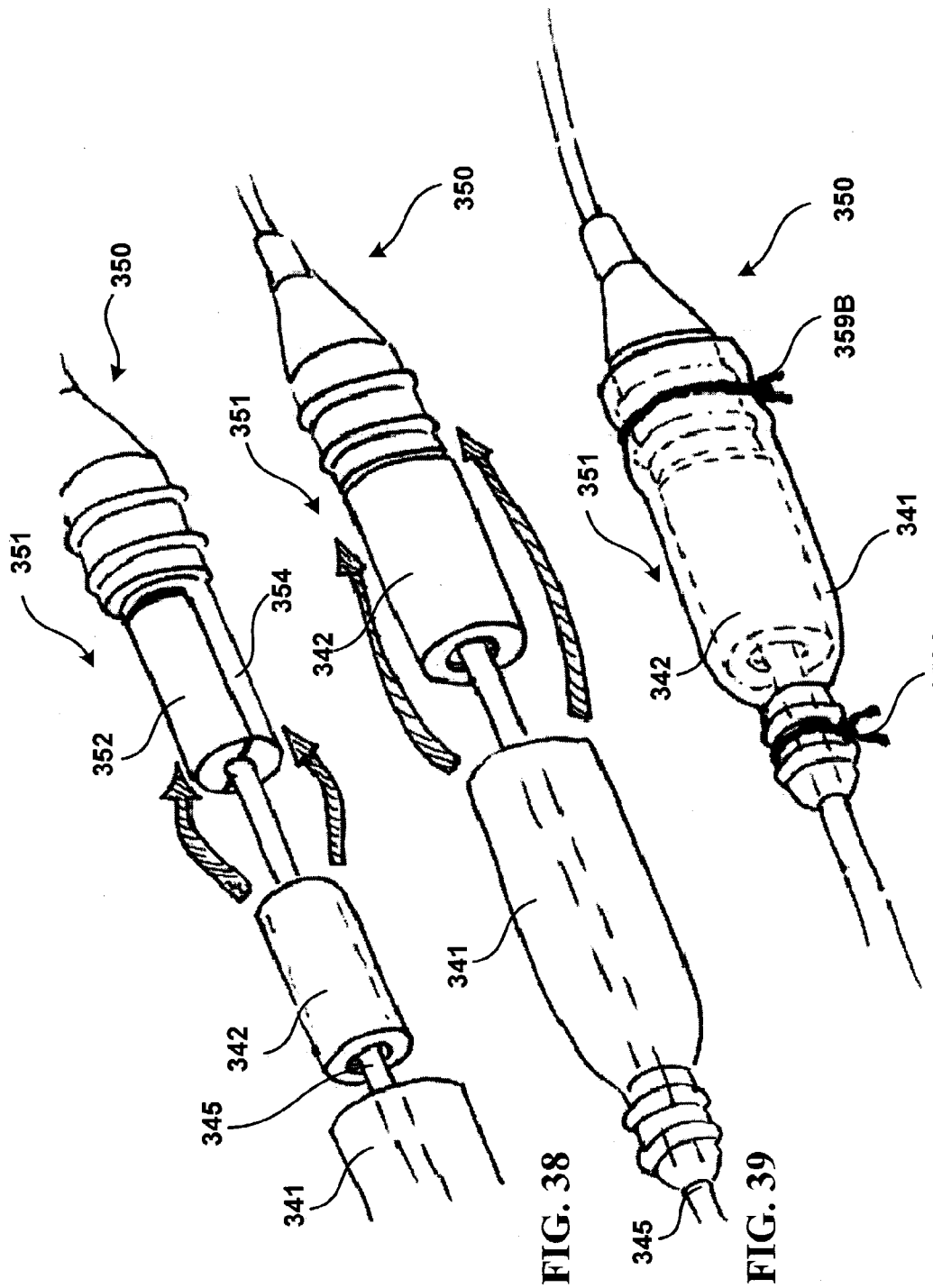

NEUROLOGICAL STIMULATION LEAD EXTENSION

FIELD OF THE INVENTION

The invention relates to neurological stimulation devices and more particularly, to neurological stimulation leads and lead extensions.

BACKGROUND OF THE INVENTION

Neurological stimulation leads refer to medical leads used to stimulate a patient's nervous system. Examples of neurological stimulation leads include spinal cord stimulation leads, deep brain stimulation leads and the like. For example, deep brain stimulation leads can be implanted at a precise location within the brain using stereotactic guidance and computed tomography (CT) or magnetic resonance imaging (MRI) techniques. Once implanted, the lead can deliver electrical stimulation to the brain in order to induce nerve impulses that inhibit symptoms of the brain disorder.

Deep brain stimulation systems typically include a pulse generator operatively connected to the implanted lead. Electrical pulses are delivered to the brain by an electrode disposed on a distal end of the implanted lead. Deep brain stimulation has been used to relieve chronic pain of neuropathic or nociceptive origin. Deep brain stimulation has also been used to treat movement disorders, such as Parkinsons Disease, as well as epilepsy and psychiatric disorders. After implanting a neurological lead, the implanted lead is often connected to a neurological lead extension, which in turn couples to the pulse generator that generates and delivers electrical pulses to a patient via the lead.

Percutaneous neurological extensions are often used immediately following implantation of a neurological lead. A percutaneous neurological extension generally refers to a temporary, non-permanent extension. Such percutaneous neurological extensions are typically used only when the patient is in the hospital under physician supervision, during which the percutaneous neurological extension may be attached to a screening cable for electrical connection to an external neurological device such as an external pulse generator or an external screener. A permanent neurological extension can replace the percutaneous neurological extension once proper operation of deep brain stimulation system has been demonstrated and verified on the patient with the temporary external system. The permanent neurological extension can be coupled to another neurological device, such as an implanted pulse generator.

Most percutaneous neurological extensions include a channel for receiving the neurological lead. Electrical contact between the extension and the lead is made in the channel. Set screws are typically inserted and/or tightened by a physician into the percutaneous neurological extension to ensure a good electrical connection between the lead and the extension and also to ensure that the lead does not dislodge from the channel of the extension.

BRIEF SUMMARY OF THE INVENTION

In general, the invention is directed to neurological lead extensions that do not require set screws or similar metallic mechanisms for lead fixation. The neurological lead extension may include a proximal end configured to couple to a neurological device and a distal end configured to couple to an implanted neurological lead. For example the proximal end may couple to an external pulse generator via coupling to a screening cable, or may couple to an implanted pulse generator.

A set of electrical contacts are disposed in proximity to the distal end to provide electrical contact to an inserted end of the implanted neurological lead. A non-metallic element may also be formed in proximity to the distal end to mechanically secure the inserted end of the implanted neurological lead to the distal end of the extension. Alternatively, or additionally, a sleeve may cover the distal end to improve mechanical retention of the lead in the extension. In this manner, the need for metallic set screws and set screw blocks and inserts can be eliminated.

In one embodiment, the invention provides a medical lead extension comprising a proximal end configured for attachment to a neurological device and a distal end formed to receive an implanted medical lead, wherein a set of electrical contacts are disposed in proximity to the distal end to contact an inserted end of the implanted medical lead. The medical lead extension may further comprise a non-metallic element formed in proximity to the distal end to mechanically secure the inserted end of the implanted medical lead to the distal end.

In another embodiment, the invention provides a medical lead extension comprising a proximal end configured for attachment to a neurological device and a distal end formed to receive an implanted medical lead, wherein a set of electrical contacts are disposed in proximity to the distal end to contact an inserted end of the implanted medical lead. The medical lead extension may further comprise a sleeve defining conduit sized to cover the distal end following insertion of the implanted medical lead in the distal end.

In another embodiment, the invention provides a medical lead assembly comprising a neurological stimulation lead and a lead extension for attachment to the neurological stimulation lead. The lead extension may include a proximal end configured for attachment to a neurological device, a distal end formed to receive the neurological stimulation lead, wherein a set of electrical contacts are disposed in proximity to the distal end to contact an inserted end of the neurological stimulation lead, and a non-metallic element formed in proximity to the distal end to mechanically secure the inserted end of the neurological stimulation lead to the distal end.

In another embodiment, the invention provides a medical lead assembly comprising a neurological stimulation lead and a lead extension for attachment to the neurological stimulation lead. The lead extension may include a proximal end configured for attachment to a neurological device, a distal end formed to receive the neurological stimulation lead, wherein a set of electrical contacts are disposed in proximity to the distal end to contact an inserted end of the neurological stimulation lead, and a sleeve defining conduit sized to cover the distal end following insertion of the neurological stimulation lead in the distal end.

In another embodiment, the invention provides a medical device comprising a neurological device, a neurological stimulation lead, and a lead extension for attaching the neurological stimulation lead to the neurological device. The lead extension may include a proximal end configured for attachment to the neurological device, a distal end formed to receive the neurological stimulation lead, wherein a set of electrical contacts are disposed in proximity to the distal end to contact an inserted end of the neurological stimulation lead, and a non-metallic element formed in proximity to the distal end to mechanically secure the inserted end of the neurological stimulation lead to the distal end.

In another embodiment, the invention provides a medical device comprising a neurological device, a neurological stimulation lead, and a lead extension for attaching the neurological stimulation lead to the neurological device. The lead extension may include a proximal end configured for attachment to the neurological device, a distal end formed to receive the neurological stimulation lead, wherein a set of electrical contacts are disposed in proximity to the distal end to contact an inserted end of the implanted medical lead, and a sleeve defining conduit sized to cover the distal end following insertion of the neurological stimulation lead in the distal end.

The different embodiments may be capable of providing a number of advantages. In particular, the invention can eliminate the need for metallic set screws and set screw blocks and inserts in medical lead extensions. By eliminating metallic set screws, the extension may be more compatible with various brain imaging or monitoring techniques such as magnetoencephalogram (MEG) imaging, which could otherwise magnetically interact with metallic set screws and inserts. Accordingly, the invention may improve patient care by allowing such brain imaging or monitoring techniques to be used on patients using a neurological stimulation system that includes an implanted lead and an extension to the implanted lead.

The elimination of set screws may also simplify the medical procedure associated with neurological stimulation by avoiding the need for a physician to insert and tighten such screws. The invention may reduce implant time and may also reduce the risk of permanent deformation of the lead by set screw tightening forces. Deformed connector end of a neurological lead may jeopardize subsequent electrical connection to a permanent neurological lead. In addition, elimination of set screws and set screw blocks and inserts may reduce costs associated with lead extension manufacture by allowing high volume, less-expensive injection molding techniques to be used for such manufacture.

The details of one or more embodiments of the invention are set forth in the accompanying drawings and the description below. Other features, objects, and advantages of the invention will be apparent from the description and drawings, and from the claims.

BRIEF DESCRIPTION OF THE DRAWINGS

FIGS. 34–40 are perspective views illustrating assembly of a neurological lead into a neurological lead extension in accordance with an embodiment of the invention.

DETAILED DESCRIPTION OF THE INVENTION

The invention is directed to various designs of neurological lead extensions that eliminate the need for metallic set screws for lead fixation. The invention may be particularly useful as a percutaneous neurological lead extension, which is a temporary, non-permanent extension, but may also find application in permanent extensions that attach to an implanted neurological device. By eliminating metallic set screws, the percutaneous neurological lead extension may be more compatible with various brain imaging or monitoring techniques such as magnetoencephalogram (MEG) imaging, which could otherwise magnetically interact with metallic set screws. Accordingly, the invention may improve patient care by allowing such brain imaging or monitoring techniques to be used on patients using a neurological stimulation system that includes an implanted lead and an extension to the implanted lead.

For example, MEG imaging is a research tool used to localize sources of electrical activity in the brain. MEG systems use a SQUID—(Superconducting QUantum Interference Device) based transducer to measure small magnetic field gradients exiting and entering the surface of the head. Some MEG systems are capable of recording magnetic activity from 64 to 142 channels over the whole head. However, MEG systems can negatively interact with metallic set screws or other metallic components of a neurological lead extension. In particular, metallic components such as set screws and set screw blocks and inserts may have sufficient mass to create undesirable magnetic moments that interfere with MEG imaging. For this reason, the invention provides designs of neurological lead extensions that eliminate metallic set screws and thereby provide improved compatibility of neurological stimulation system and MEG systems or other brain monitoring or imaging systems. The lead extensions described herein may be substantially non-metallic, and substantially non-ferromagnetic, allowing the lead to be more compatible with MEG imaging.

Figure 1:
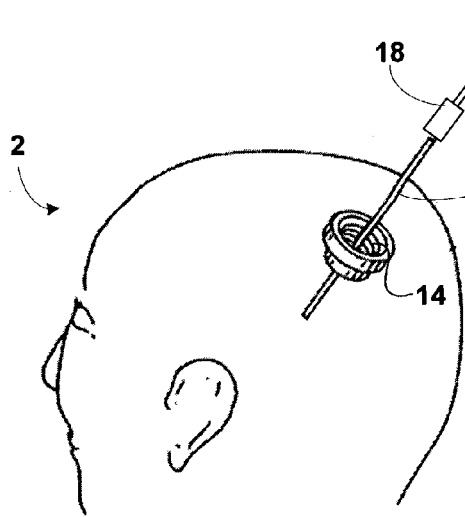
FIG. 1 is a conceptual view of a patient having a neurological lead implanted into the patient's brain via a burr hole in the patient's cranium.

FIG. 1 is a conceptual view of a patient 2 having a neurological lead 10 implanted into the patient's brain via a burr hole 14 in the patient's cranium. For example, lead 10 can be implanted within the patient's brain using stereotactic guidance and CT or MRI techniques, as known in the art. Following insertion of neurological lead 10, lead 10 can be coupled to neurological lead extension 16 as outlined in greater detail below. Neurological lead extension 16 may define a proximal end 17 configured to couple to a neurological device such as a pulse generator, a screener, or the like. In some cases, proximal end 17 may couple to a cable, that in turn couples to the neurological device. Distal end 18 is configured to couple to lead 10. As outlined in greater detail below, neurological lead extension 16 may coupled to lead 10 at distal end 18 without the use of set screws.

Figure 2:
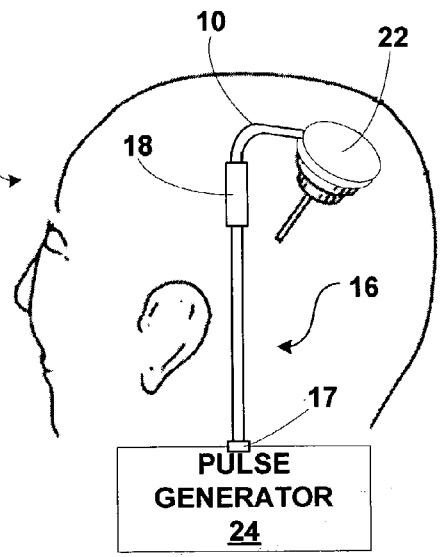
FIG. 2 is another conceptual view of a patient having a neurological lead implanted into the patient's brain via a burr hole in the patient's cranium.

FIG. 2 is another conceptual view of a patient 2 having a neurological lead 10 implanted into the patient's brain via a burr hole in the patients cranium. As shown in FIG. 2, a burr hole cap 22 covers the burr hole following insertion of lead 110. Lead 10 is coupled to neurological lead extension 16 at distal end 18, without the use of set screws. The proximal end 17 of neurological lead extension 16 is then coupled to a neurological device such as a pulse generator 24, which provides therapeutic stimulation pulses to the patient's brain via extension 16 and lead 10. Neurological lead extension 16 may comprise a percutaneous neurological extension, which is a temporary, non-permanent extension. In that case, a permanent neurological extension can replace the percutaneous neurological extension once proper operation of deep brain stimulation system has been demonstrated and verified on the patient.

Figure 3:
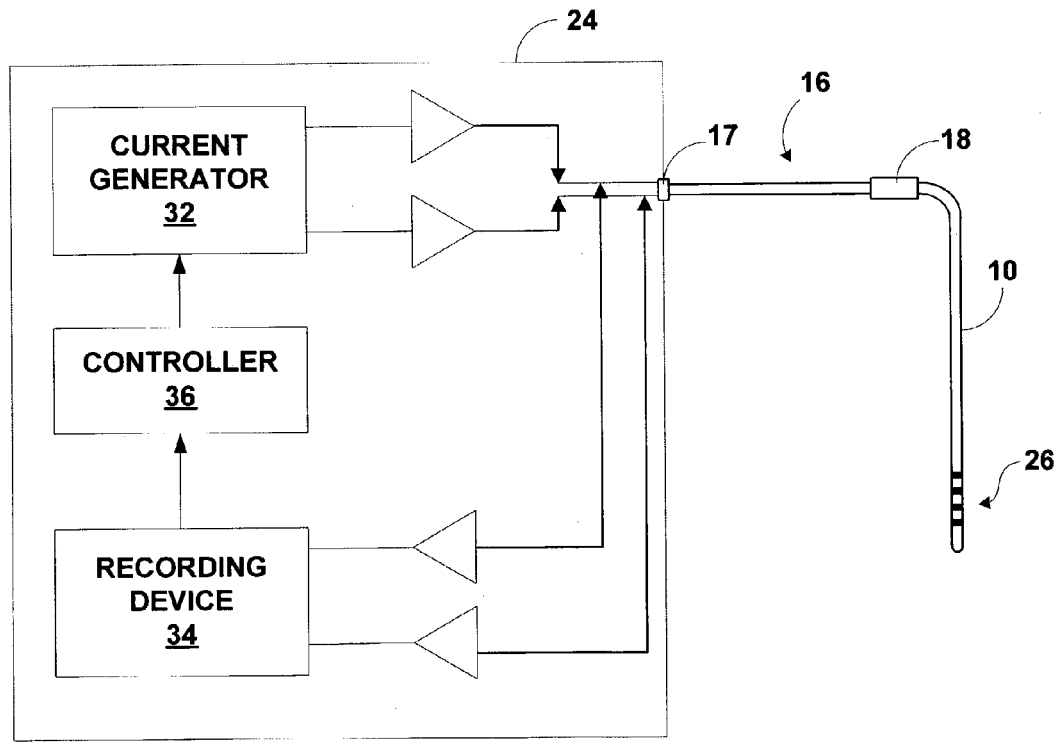
FIG. 3 is a functional block diagram illustrating an exemplary pulse generator.

FIG. 3 is a functional block diagram illustrating an exemplary pulse generator 24 in greater detail. As shown in FIG. 3, pulse generator 24 may couple to proximal end 17 of neurological lead extension 16. In particular, proximal end 17 may be specifically configured for attachment to pulse generator 24. Distal end 18 is configured for attachment to neurological lead 10 without the use of set screws. In the illustrated example of FIG. 3, neurological lead 10 includes a plurality electrodes 26 disposed on a distal end of lead 10 to deliver to a patient's brain the electrical stimuli produced by pulse generator 24.

Pulse generator 24 may include current generator 32, a recording device 34, and a controller 36. In operation, recording device 34 records signals obtained from one or more electrodes 26 carried by lead 10. The recorded signals may be used for analysis, triggering of current generator 32 or both. For example, controller 36 may be responsive to brain activity signals sensed by recording device 34 via lead 10, and thereby activate current generator 32 to deliver electrical stimuli to one or more electrodes 26 carried by lead 10.

In the example of FIG. 3, two conductors are shown. However, the number of conductors, and associated sensing and current output channels, may vary. Pulse generator 24 may be, for example, a Medtronic Model 3628, or a modification of that device. Controller 36 may utilize a microprocessor and/or other control and timing circuitry. In addition, controller 36 may control switching circuitry to switch the output of current generator 32 between different conductors that carry stimulation current to electrodes 26 of lead 10.

Lead extension 16 couples lead 10 to pulse generator 24, or another type of neurological device. One challenge in the design of lead extension 16 relates to the coupling between lead 10 and lead extension 16 at distal end 18 of lead extension 16. In particular, lead 10 must be electrically and mechanically coupled to extension 16 in a manner that ensures robust operation of the neurological stimulation system. Conventionally, set screws are used at distal end 18 for fixation following insertion of lead 10 into distal end 18. For example, conventional metallic set screws can help ensure a robust electrical connection between extension 16 and lead 10, and can also provide mechanical strength at the attachment.

Set screws, however, present a number of problems to the neurological stimulation system. For example, insertion of set screws can be a trying task for a physician, adding complexity to the medical procedure. Also, over tightening of set screws can cause lead damage that can undermine connection to a permanently implanted pulse generator. In addition, metallic set screws may be incompatible with various brain monitoring or brain imaging techniques that may be desirable to perform on a patient using a neurological stimulation system. For example MEG systems can negatively interact with metallic set screws and set screw blocks and inserts of a neurological lead extension. For these reasons, as outlined in greater detail below, the invention provides designs of neurological lead extensions that eliminate metallic set screws. Thus, the invention can simplify the medical procedure associated with implantation of neurological leads, possibly reducing implant time, and may provide improved compatibility of neurological stimulation system and MEG systems or other brain monitoring or imaging systems.

Figure 61:
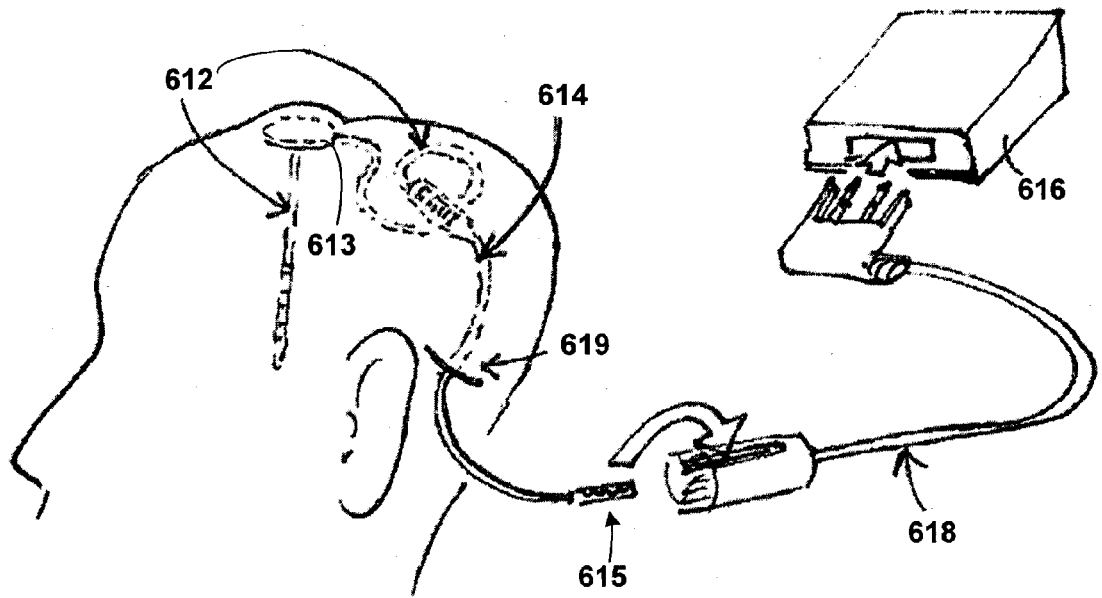
FIG. 61 is a conceptual view of a patient having a neurological lead implanted into the patient's brain via a burr hole in the patient's cranium, with the lead being attached to a percutaneous extension that attaches to an external neurological device via a cable.

FIG. 61 is another conceptual view of a patient having a neurological lead 612 implanted into the patient's brain via a burr hole in the patients cranium. As shown in FIG. 61, a burr hole cap 613 covers the burr hole following insertion of lead 612. Lead 612 is coupled to a percutaneous neurological lead extension 614, without the use of set screws. Percutaneous neurological lead extension 614 may exit from the patient through slit 619. Proximal end 615 of percutaneous neurological lead extension 614 is then coupled to a neurological device 616 such as an external pulse generator or screener. In particular, proximal end 615 of percutaneous neurological lead extension 614 may be configured to couple to cable 618, e.g., in a twist-locking manner to allow for electrical connection to device 616.

Percutaneous neurological extension 614 generally refers to a temporary, non-permanent extension. Such percutaneous neurological extensions are typically used only when the patient is in the hospital under physician supervision, during which the percutaneous neurological extension 614 may be attached to cable 618 for electrical connection to neurological device 616. A permanent neurological extension can replace percutaneous neurological extension 614 once proper operation of deep brain stimulation system has been demonstrated and verified on the patient with the temporary external system. As used in this disclosure, the phase "configured for attachment to a neurological device" refers to direct attachment to an external or implanted neurological device, or attachment to a cable, or the like, that in turn attaches the extension to such an implanted or external neurological device.

Figure 62:
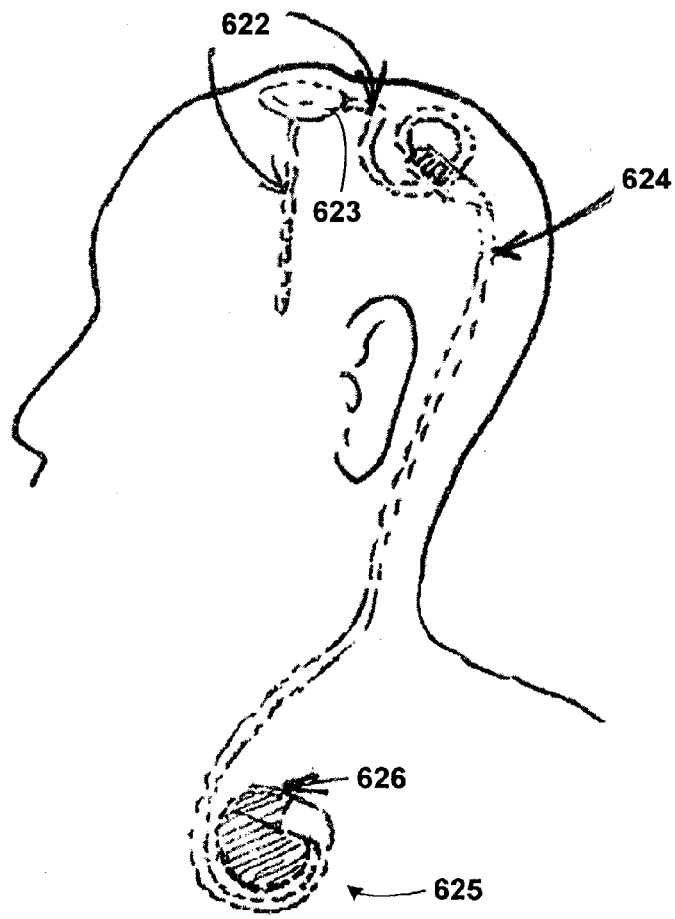
FIG. 62 is a conceptual view of a patient having a neurological lead implanted into the patient's brain via a burr hole in the patient's cranium, with the lead being attached to a permanent extension that attaches to an implanted neurological device.

FIG. 62 is another conceptual view of a patient having a neurological lead 622 implanted into the patient's brain via a burr hole in the patients cranium. As shown in FIG. 62, a burr hole cap 623 covers the burr hole following insertion of lead 622. In this case, lead 622 is coupled to a permanent lead extension 624, without the use of set screws. The proximal end 625 of permanent neurological lead extension 624 is then coupled to a neurological device 626 such as an implanted pulse generator. In particular, proximal end 625 of permanent neurological lead extension 624 may be configured to couple to device 626.

Figure 4:
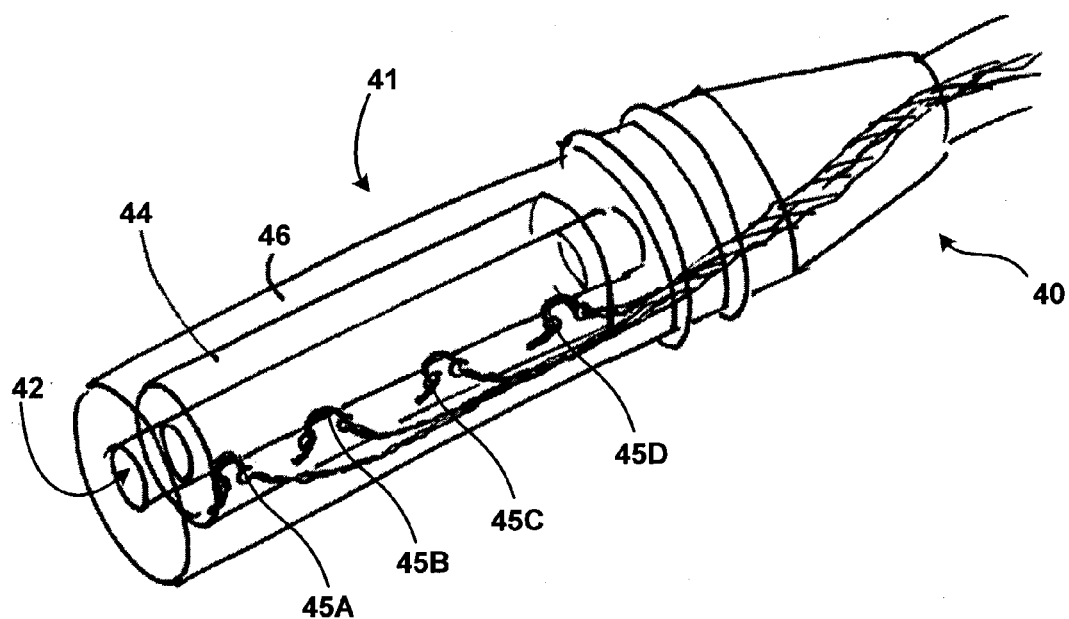
FIG. 4 is an exemplary perspective view of one embodiment of a neurological lead extension.

FIG. 4 is an exemplary perspective view of one embodiment of a neurological lead extension 40, which may correspond to extension 10 of FIGS. 1–3, extension 614 of FIG. 61 or extension 624 of FIG. 62. In particular, FIG. 4 illustrates the distal end 41 of extension 40 in detail, e.g., the connector end that couples to a medical lead. The other end, i.e., the proximal end (not shown) is configured to couple to a neurological device, such as an external or internal device either directly or via a cable. In this embodiment, distal end forms a bore 42 sized to receive a neurological lead. Distal end 41 may comprise a hard plastic component 44 that defines bore 42 and a silicone rubber housing 46 that surrounds component 44. A set of electrical contacts 45A–45D (collectively electrical contacts 45) are disposed within bore 42 to provide electrical connection to an inserted medical lead, e.g., an in-line lead that includes a plurality of electrical contacts along its major axis.

Electrical contacts 45 may comprise wires positioned or formed within component 44 such that contacts 45 provide a desired level of resistance to insertion of a lead into bore 42. In that case, contacts 45 may bias against electrical contacts of an inserted lead with sufficient force to inhibit accidental retraction of an inserted lead. In other words, contacts 45 may electrically contact an inserted lead, and may also provide frictional force that tends to hold the lead within bore. As described in greater detail below, certain additional elements may be added to an extension to improve and stabilize the mechanical coupling between an inserted lead and the extension.

Figure 5:
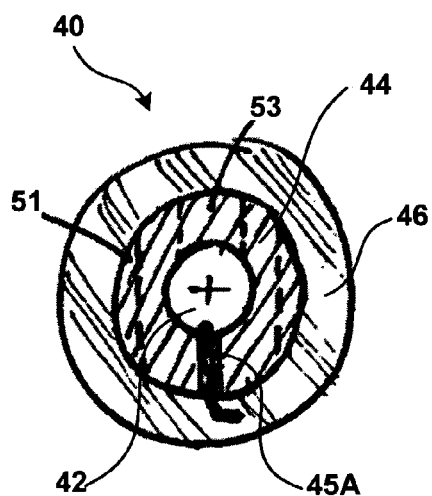
FIG. 5 is a cross-sectional front view of neurological lead extension.

FIG. 5 is a cross-sectional front view of neurological lead extension 40, illustrating bore 42, a hard plastic component 44 that defines bore 42, and a silicone rubber housing 46 that surrounds component 44. If desired, sides 51A, 51B of component 44 may be flat for improved fixation when embedded within a silicone housing 46. Also, an optional perpendicular hole 53 may be added for manufacturing purposes, e.g., to allow access to contacts 45 and facilitate wire routing through component 44.

Figure 6:
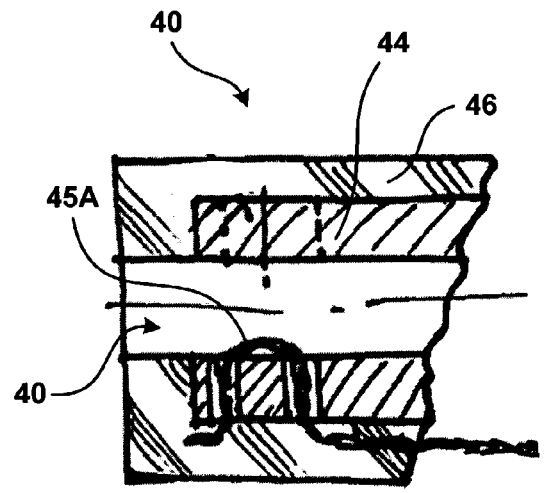
FIG. 6 is a cross-sectional side view of a portion of a distal end of a neurological lead extension that couples to a neurological lead.

FIG. 6 is a cross-sectional side view of a portion of distal end 41 of neurological lead extension 40, illustrating bore 42, hard plastic component 44 that defines bore 42, and a silicone rubber housing 46 that surrounds component 44. Also illustrated in FIG. 6 is one contact area 45A routed through component 44 and embedded in silicone rubber housing 46. Materials other than hard plastic and silicone rubber could also be used to realize a neurological lead extensions in accordance with the invention, although non-metallic materials are preferred because the elimination or reduction of metal and ferromagnetic material makes the extension more compatible with brain imaging and brain monitoring procedures.

Figure 7:
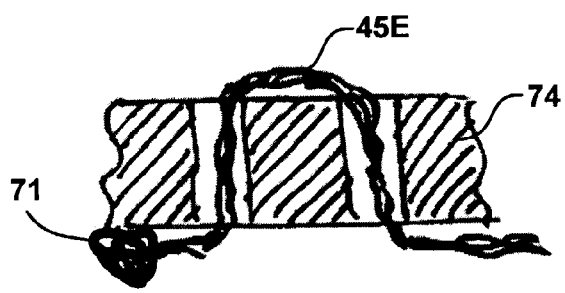
FIGS. 7, 8 and 9 illustrate three exemplary electrical contacts that can be used on neurological lead extensions.
Figure 8:
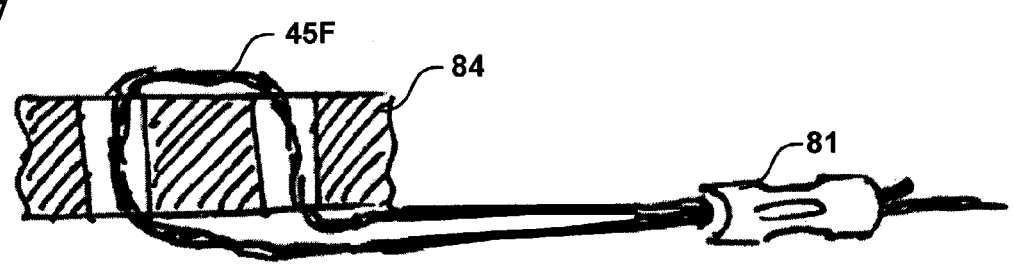
Figure 9:
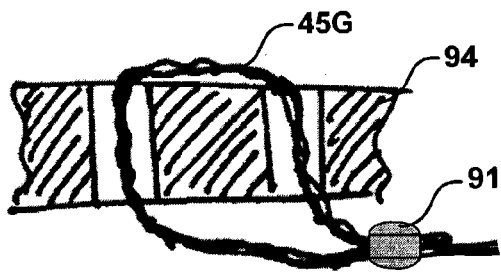

FIGS. 7, 8 and 9 illustrate three exemplary electrical contacts 45E, 45F, 45G which may correspond to contacts 45 of FIGS. 4–6 or similar contacts of other embodiments described below. As shown in FIG. 7, contact 45E comprises a wire formed with a knot 71 that ensures that the wire cannot retract through one or more holes in hard plastic component 74. Knot 71 may also be embedded in silicone rubber during manufacturing to further ensure stability. As shown in FIG. 8, contact 45F comprises a wire routed through holes in hard plastic component 84. In FIG. 8, a crimp 81 is added to secure the wire. As shown in FIG. 9, contact 45G comprises a wire routed through holes in hard plastic component 94. In FIG. 9, a weld 91 is added to secure the wire.

Figure 10:
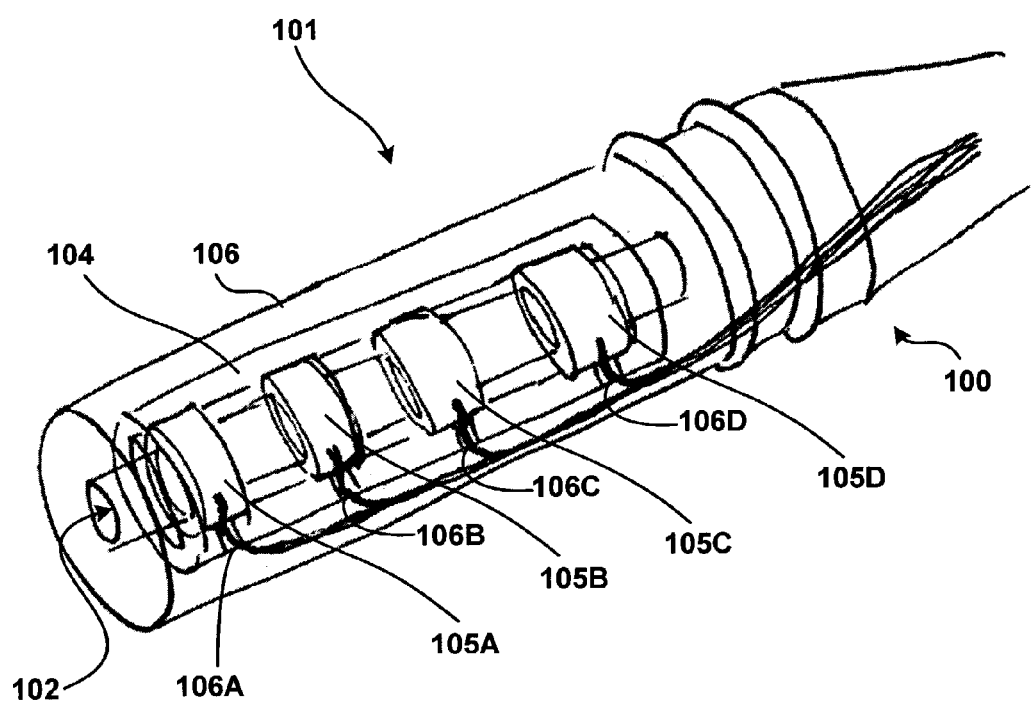
FIG. 10 is a perspective view of another embodiment of a neurological lead extension having multi-beam contacts similar to those used on bipolar implantable pulse generator (IPG) connectors.

FIG. 10 is an exemplary perspective view of another embodiment of a neurological lead extension 100, which may correspond to the extensions of FIGS. 1–3, 61 or 62. FIG. 10 illustrates the distal end 101 of extension 100 in detail, e.g., the connector end that couples to a medical lead. The other end, i.e., the proximal end (not shown), is configured to couple to a neurological device either directly or indirectly via a cable. In this embodiment, distal end 101 forms a bore 102 sized to receive a neurological lead. Distal end 101 may comprise a hard plastic component 104 that defines bore 102 and a silicone rubber housing 106 that surrounds component 104. A set of electrical contacts 105A–105D (collectively electrical contacts 105) are disposed within bore 102 to provide electrical connection to an inserted medical lead, e.g., an in-line lead that includes a plurality of electrical contacts along its major axis. In other words, contacts 105 may comprise multi-beam contacts similar to those commonly used in in-line bipolar cardio-rhythm management (CRM) implantable pulse generator (IPG) headers. In this case, electrical contacts 105 comprise conductive rings attached to routed wires 106A–106D that are routed through component 104 and housing 106. Component 104, could optionally be eliminated in some embodiments.

Figure 11:
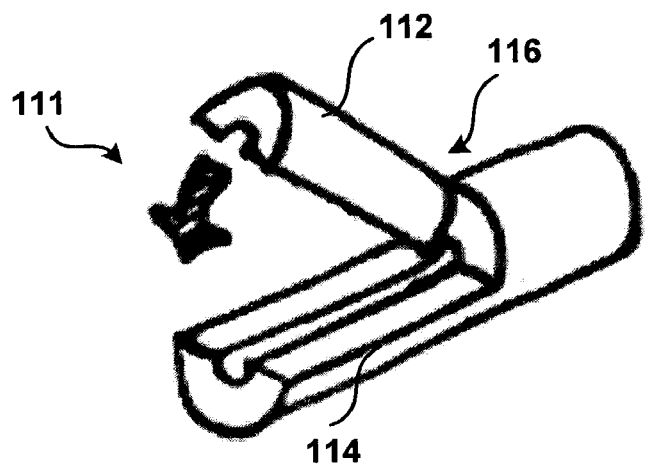
FIG. 11 is a perspective view of another exemplary distal end of a neurological lead extension that couples to a neurological lead.

FIG. 11 is a perspective view of another exemplary distal end of a neurological lead extension, e.g., the connector end that couples to a neurological lead. In this case, distal end 111 comprises a top portion 112 and a bottom portion 114 that fit together or otherwise assemble to form a bore. For example, top portion 112 and bottom portion 114 may comprise separate pieces, or may be hinged together, e.g., at 116. Such hinging can reduce the number of components, and particularly reduce the number of loose components, e.g., inside packaging.

Figure 12:
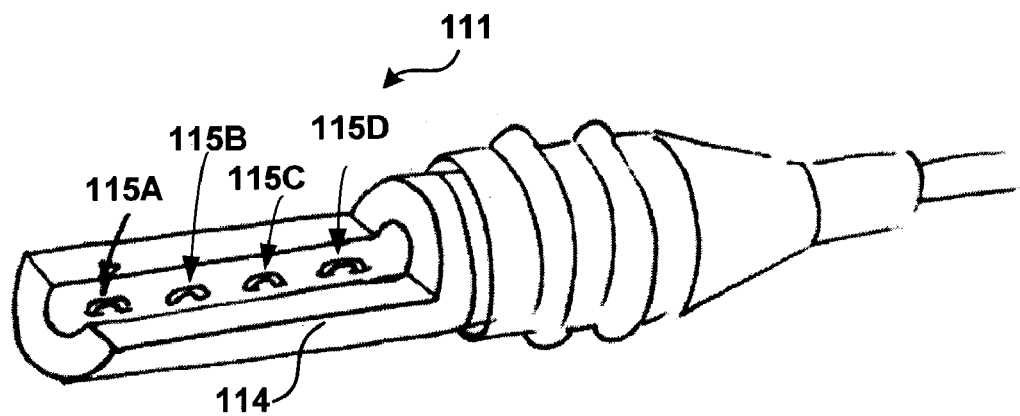
FIG. 12 is a perspective view of a bottom portion of a distal end of a neurological lead extension that couples to a neurological lead.
Figure 13:
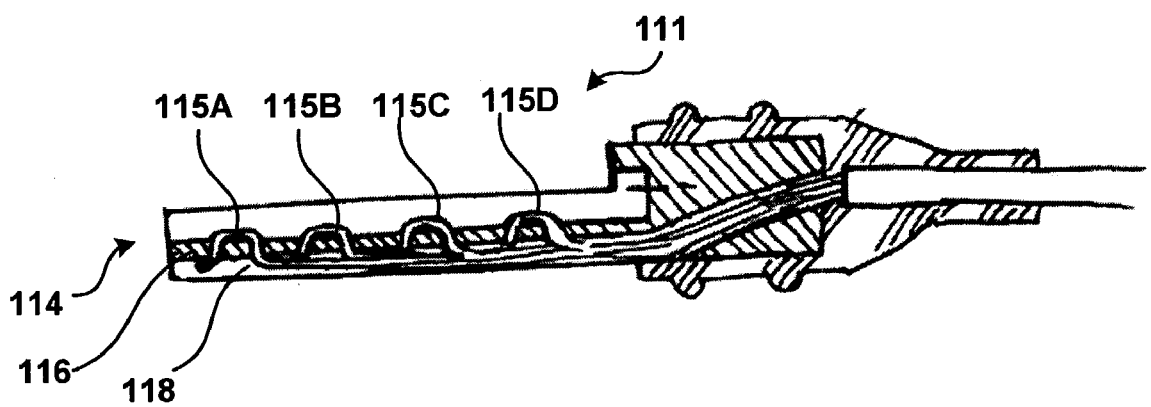
FIG. 13 is a cross-sectional side view of the bottom portion of the extension illustrated in FIG. 12.

FIG. 12 is a perspective view of distal end 111 showing only bottom portion 114, and FIG. 13 is a cross-sectional side view of bottom portion 114. As shown in FIGS. 12 and 13, distal end 111 electrical contacts 115A–115D formed in bottom portion 114 similar to a manner described above. For example, bottom portion 114 may include a hard plastic component 116 through which wires are routed to form contacts 115. A silicone rubber housing 118 may surround or hold component 116 and seal the wires in place. An adhesive or the like, may also be used. The wires that form contacts 115 could also be positioned perpendicular to the body of extension, if desired.

Figure 14:
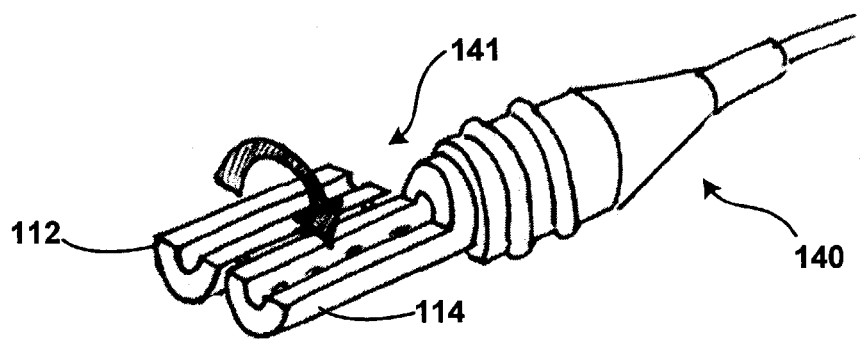
FIG. 14 is a perspective view of a distal end of a neurological lead extension that couples to a neurological lead including top and bottom portions in a hinged configuration to avoid separate loose components and ease of the implant procedure.

FIG. 14 is a perspective view of a distal end 141 of a neurological lead extension 140 including top and bottom portions 112, 114 in a hinged configuration. Such a hinged configuration can simplify the medical procedure by avoiding loss or misplacement of top portion 112.

Figure 15:
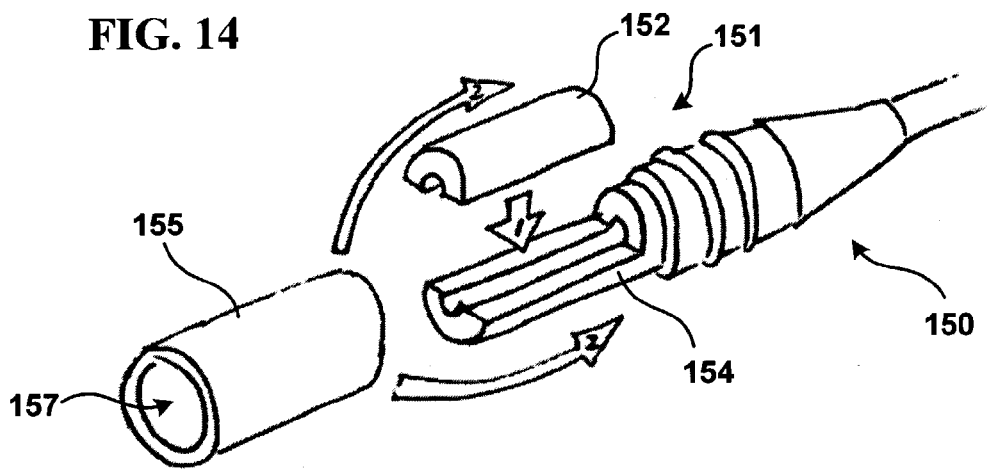
FIG. 15 is another perspective view of a distal end of a neurological lead extension that couples to a neurological lead including separate top and bottom portions

FIG. 15 is another perspective view of a distal end 151 of a neurological lead extension 150 including separate top and bottom portions 152, 154. Also shown in FIG. 15 is a sleeve 155 that can fit over top and bottom portions following assembly of the top and bottom portions 152, 154 about a neurological lead (not shown). In other words, top and bottom portions 152, 154 can fit together about a lead to form a bore that surrounds the lead and causes electrical contact between the lead and contact areas in bottom portion 154. Sleeve 155 defines a conduit 157 sized so that sleeve 155 can snugly fit over the top and bottom portions 152, 154 to hold them against one another. In some cases, top and bottom portions 152, 154 may be tapered, or formed with optional flat sides to allow for simplified insertion of sleeve 155 about top and bottom portions 152, 154.

Figure 16:
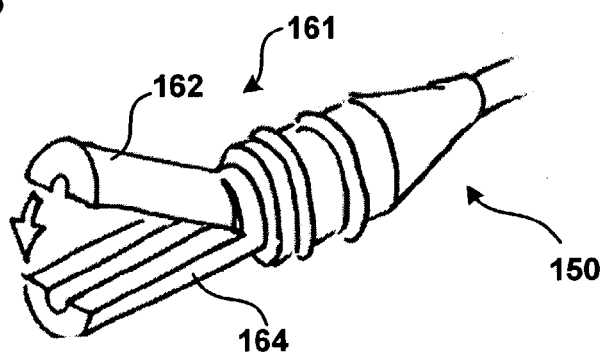
FIGS. 16–18 are additional perspective views of distal ends of neurological lead extensions including hinged top and bottom portions.
Figure 17:
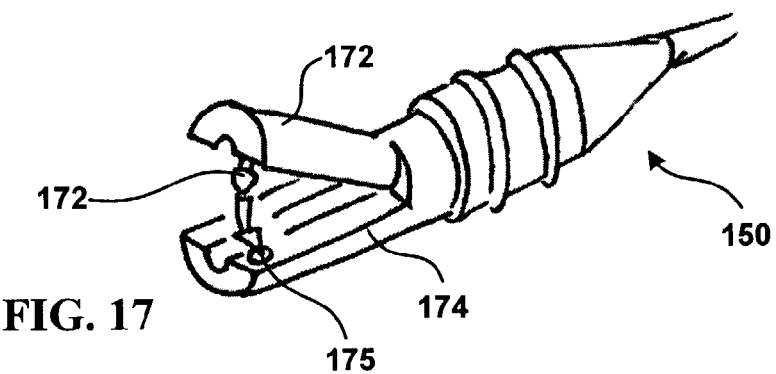

FIGS. 16 and 17 are additional perspective views of distal ends 161, 171 of neurological lead extensions 160, 170 including hinged top portions 162, 172 and bottom portions 164, 174. As shown in FIG. 17, top portion 172 may also include a protrusion 173 that mates with hole 175 of bottom portion, e.g., in a snap-fit configuration. Alternatively, the protrusion may be formed on the bottom portion 174 and the hole may be formed on top portion 172.

Figure 18:
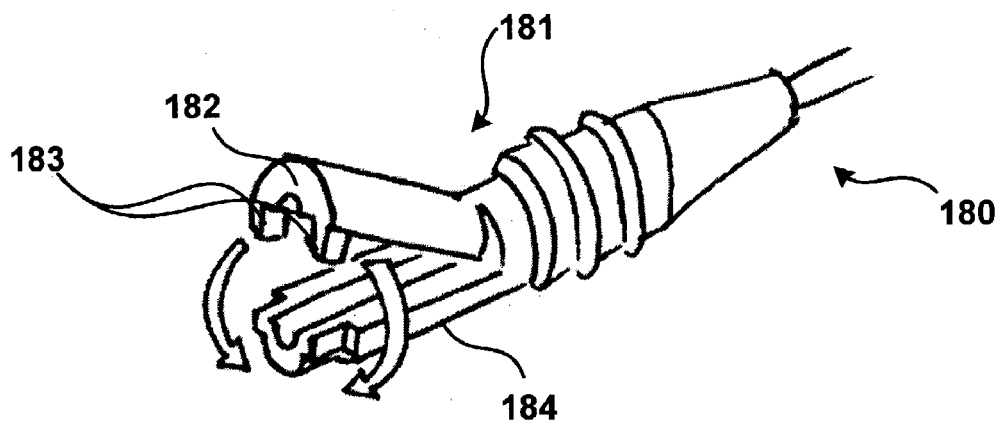

FIG. 18 is another perspective view of a distal end 181 of a neurological lead extension 180 including hinged top and bottom portions 182, 184. As shown in FIG. 18 top portion 182 may include molded features 183 that snap fit with bottom portion 184, or vice versa.

Figure 19:
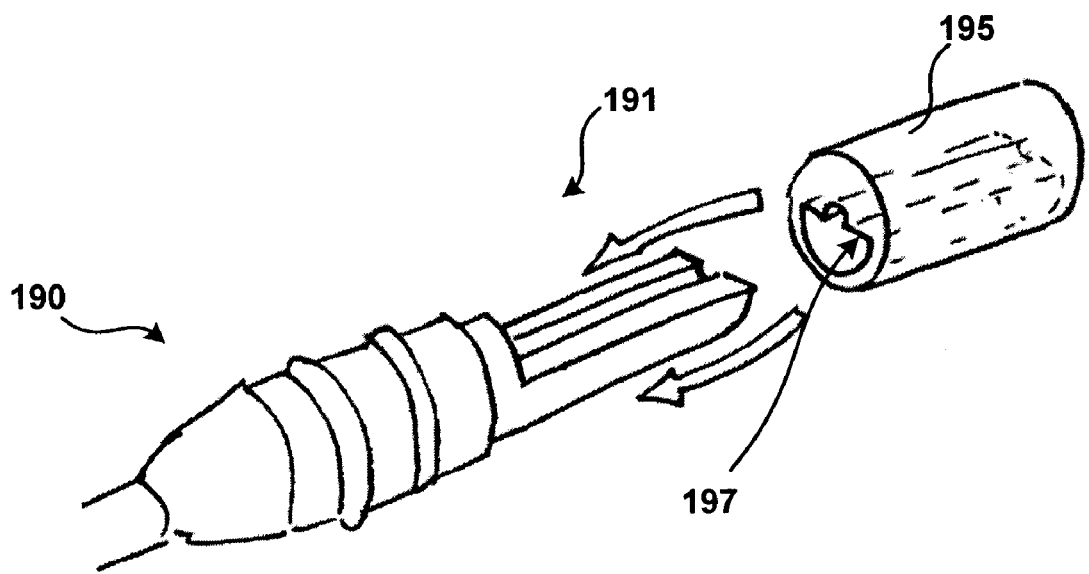
FIG. 19 is another perspective view of a distal end of a neurological lead extension that couples to a neurological lead.

FIG. 19 is another perspective view of a distal end 191 of a neurological lead extension 190. In FIG. 19, the top portion is eliminated, and instead sleeve 195 is specifically molded to define a conduit 197 sized and shaped to corresponding to bottom portion 194 and an inserted lead (not shown). Thus, following insertion of lead into channel 196 of bottom portion 194, sleeve 195 can be placed over bottom portion to secure lead in channel 196. In that case, electrical contact between the lead and extension 190 would occur in channel 196 in a manner similar to that described above for other embodiments.

Figure 20:
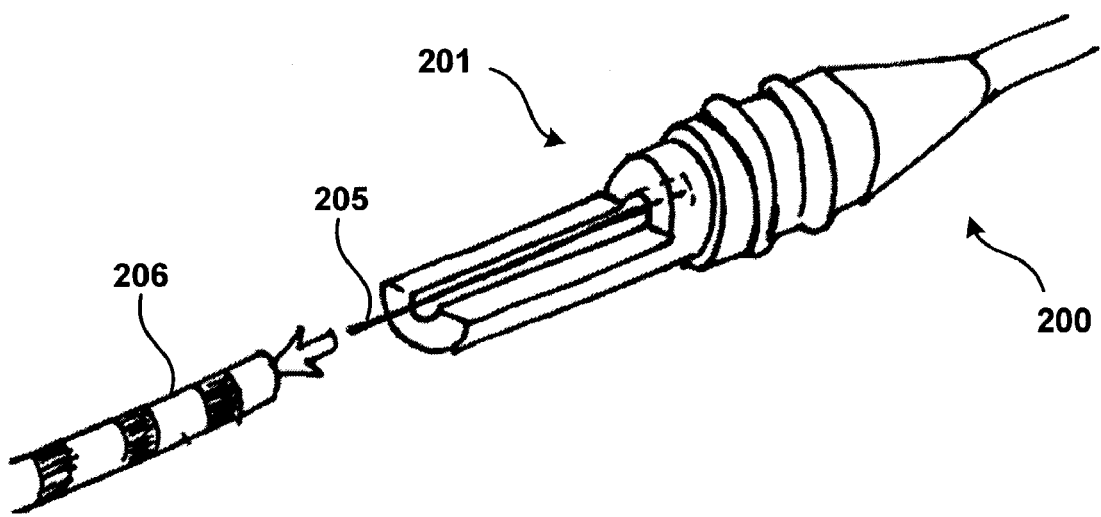
FIG. 20 is another perspective view of a distal end of a neurological lead extension that couples to a neurological lead with a short stylet running into an open lumen of the extension to hold the extension in place during the implant procedure.
Figure 21:
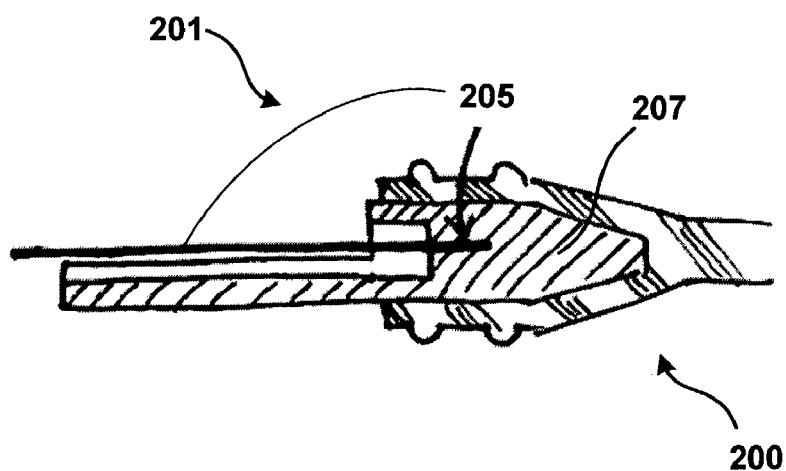
FIG. 21 is a cross-sectional side view of the extension illustrated in FIG. 20.

FIG. 20 is another perspective view of a distal end 201 of a neurological lead extension 200 (again, the distal end being the end that couples to a neurological lead). FIG. 21 is a cross-sectional side view. As shown in FIGS. 20 and 21, a stylet 205 may be included in the channel or bore of distal end 201, e.g., to guide lead 206 to the proper location inside the female extension connector and hold in place during assembly of the lead extension by a physician. For example stylet 205 may be embedded in material 207, e.g. silicone rubber, during manufacture of lead extension 200. Stylet 205 may be sufficiently short to ensure that it mates with the connector area only, i.e., the distal end of lead extension 200.

Figure 22:
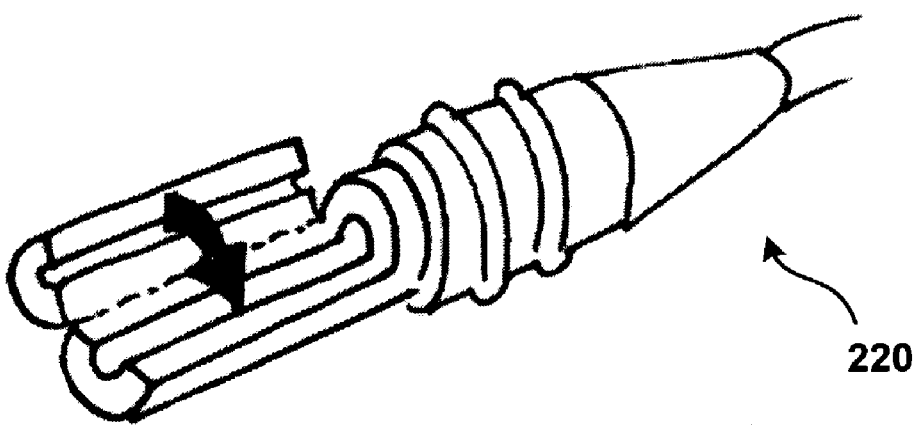
FIGS. 22 and 23 additional perspective views of distal ends of a neurological lead extensions having hinged configurations.
Figure 23:
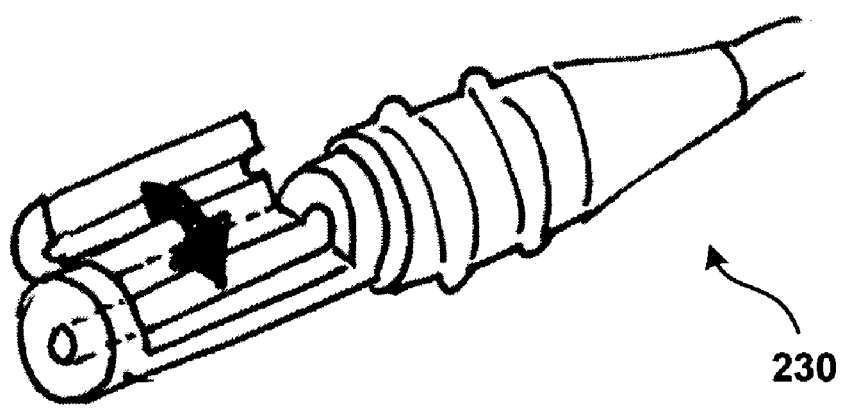

FIGS. 22 and 23 are additional perspective views of a distal ends of a neurological lead extensions 220 and 230 having hinged configurations. Lead 230 may also hold a medical lead in place in the connector assembly process during the implant procedure, and may therefore perform similar functions to a guide wire or stylet.

Figure 24:
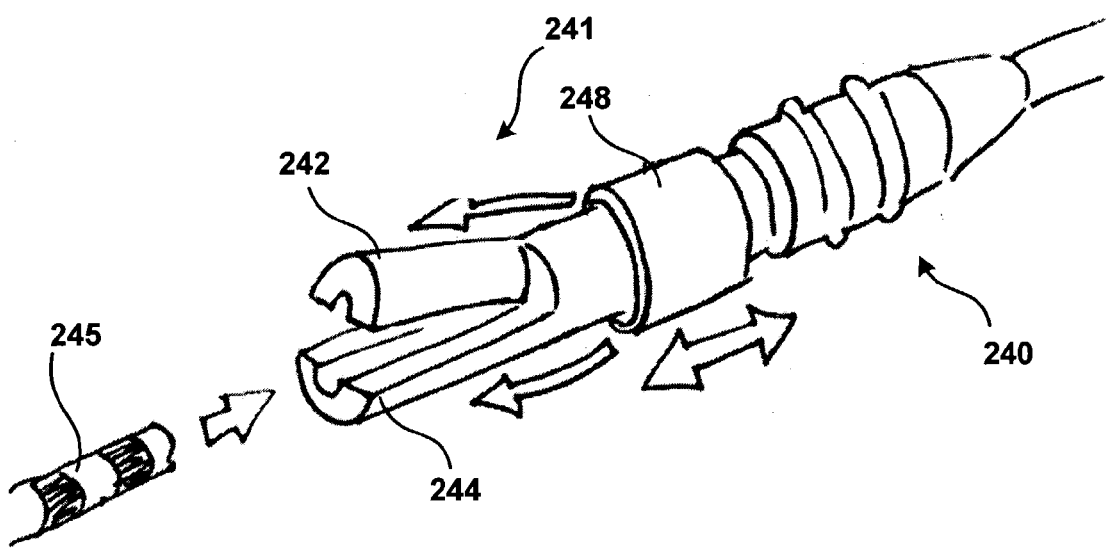
FIGS. 24 and 25 are additional perspective views of a distal end of a neurological lead extension having a hinged configuration.
Figure 25:
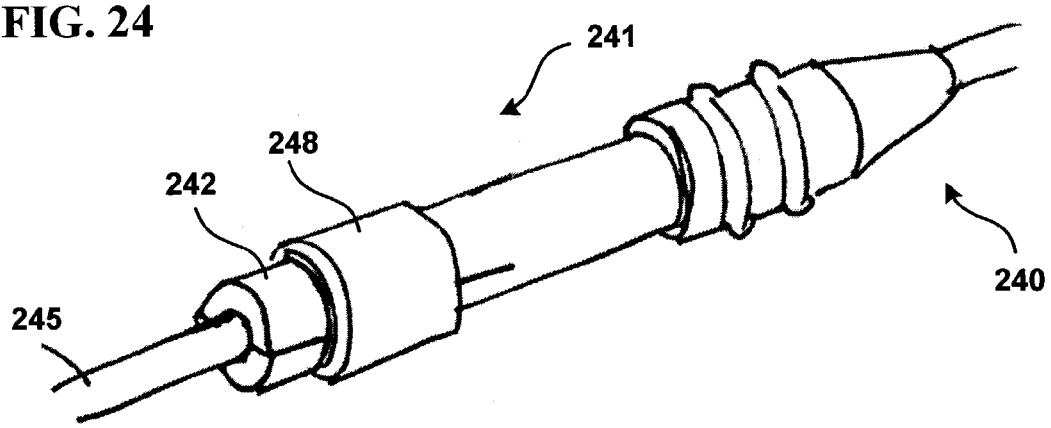

FIGS. 24 and 25 are additional perspective views of a distal end 241 of a neurological lead extension 240 having a hinged configuration. As shown in FIG. 24, following insertion of lead 245 and assembly of top and bottom portions 242, 244 about lead 245, sleeve 248 can be slid or otherwise fitted about top and bottom portions 242, 244 to secure lead 245 in place. In particular, sleeve 248 may define a conduit that is sized to fit about top and bottom portions 242, 244, e.g., in a substantially snug manner in order to secure lead 245 in place.

Figure 26:
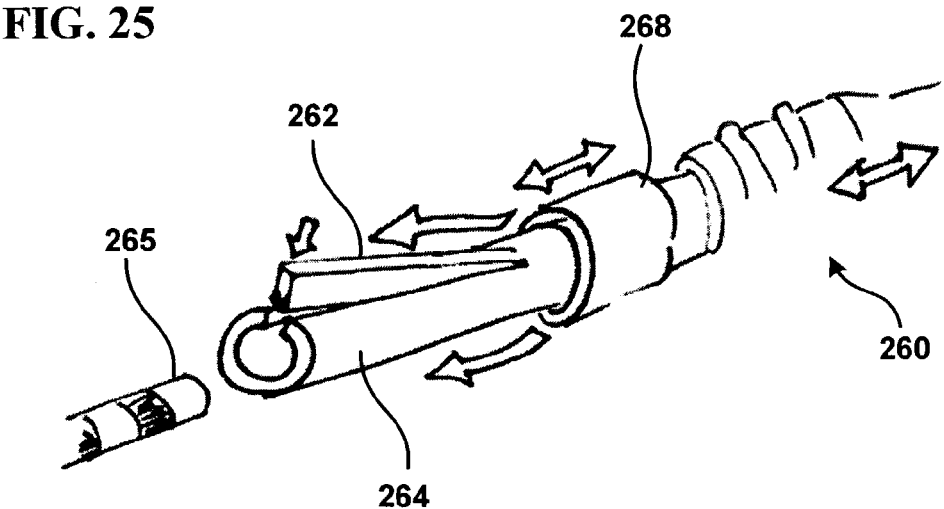
FIG. 26 is another perspective view of a distal end of a neurological lead extension having a hinged configuration and a sleeve that fits around top and bottom portions following assembly about lead.

FIG. 26 is another perspective view of a distal end of a neurological lead extension 260 having a hinged configuration and a sleeve 268 that fits around top and bottom portions 262, 264 following assembly about lead 265.

Figure 27:
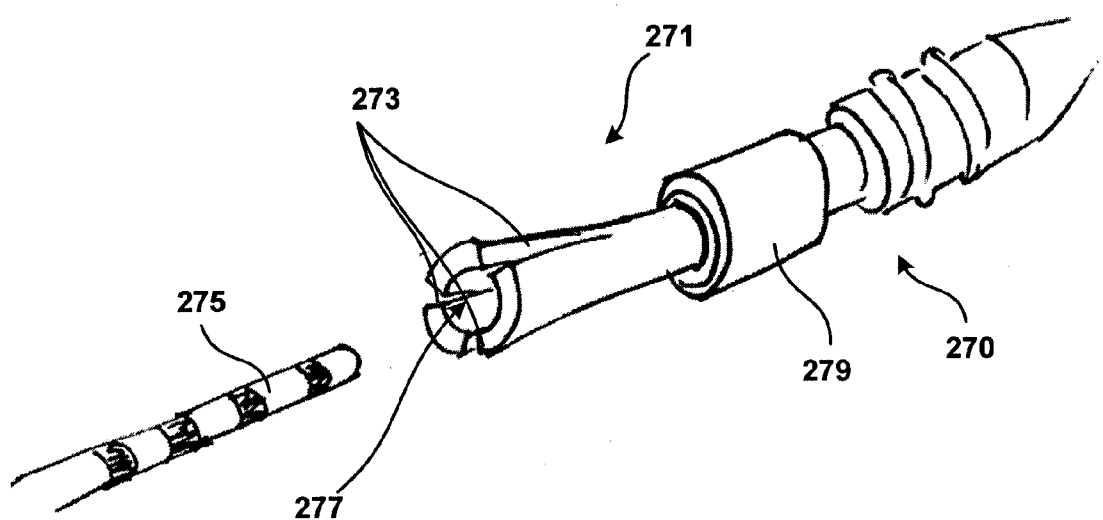
FIG. 27 is another perspective view of a distal end of a neurological lead extension.

FIG. 27 is another perspective view of a distal end 271 of a neurological lead extension 270. In this case, distal end 271 defines slits 273 that enable easy insertion of lead 275 into bore 277 in a manner similar to a cotter bolt structure. Sleeve 279 can then be positioned over distal end 271 to secure lead 275 within bore 277, and may come from either the front or back of extension 270. Sleeve 279 may define a conduit sized to fit tightly around distal end 271 following insertion of lead 275 into bore 277. In this manner, lead can be securely fit within bore 277 without the use of set screws.

Figure 28:
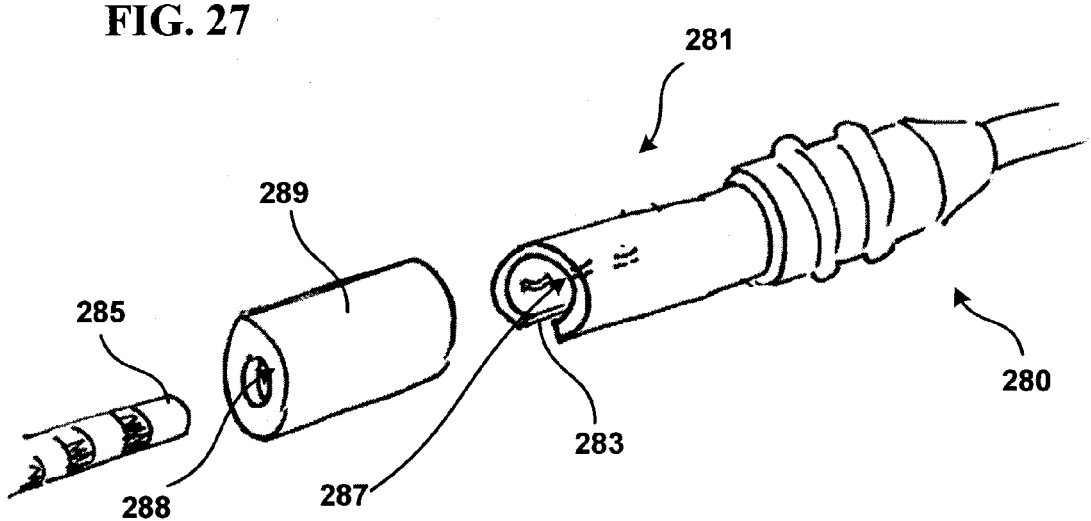
FIG. 28 is a perspective view of a distal end of a neurological lead extension having a slitted configuration.

FIG. 28 is another perspective view of a distal end 281 of a neurological lead extension 280 having a slitted configuration. In this case, distal end 281 defines a single slit 283 that enables easy insertion of lead 285 into bore 277. Sleeve 289 can then be positioned over distal end 281 to secure lead 285 within bore 287. In particular, sleeve 289 may define a conduit 288 sized to fit tightly around distal end 281 following insertion of lead 285 into bore 287. In this manner, lead can be securely fit within bore 287 without the use of set screws.

Figure 29:
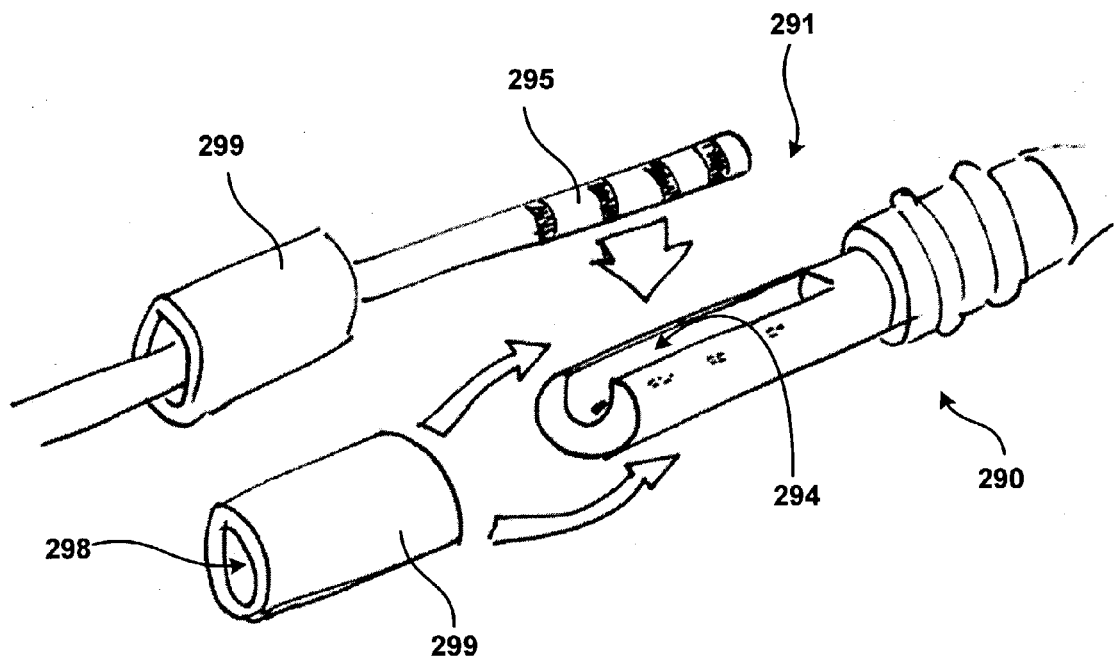
FIG. 29 is another perspective view of a distal end of a neurological lead extension.

FIG. 29 is another perspective view of a distal end 291 of a neurological lead extension 290. In this case, distal end 291 defines a channel 294 sized to receive lead 295. Then following insertion of lead 295 into channel 294, sleeve 299 can then be positioned over distal end 291 to secure lead 295 within channel 294. Sleeve 299 may define a conduit 298 sized to fit tightly around distal end 291 following insertion of lead 295 into channel 294.

Figure 30:
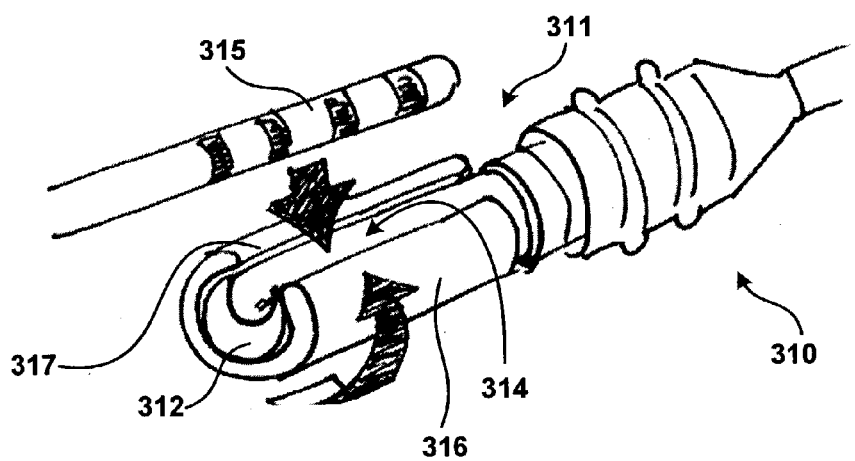
FIG. 30 is another perspective view of a distal end of a neurological lead extension.
Figure 31:
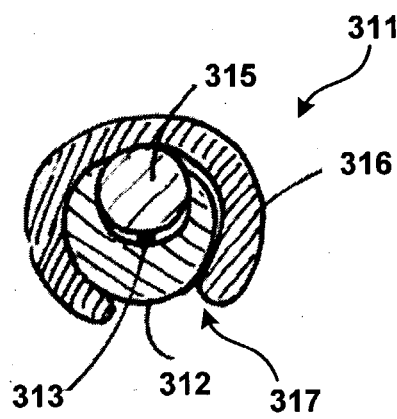
FIG. 31 is a cross-sectional view of the extension illustrated in FIG. 30.
Figure 32:
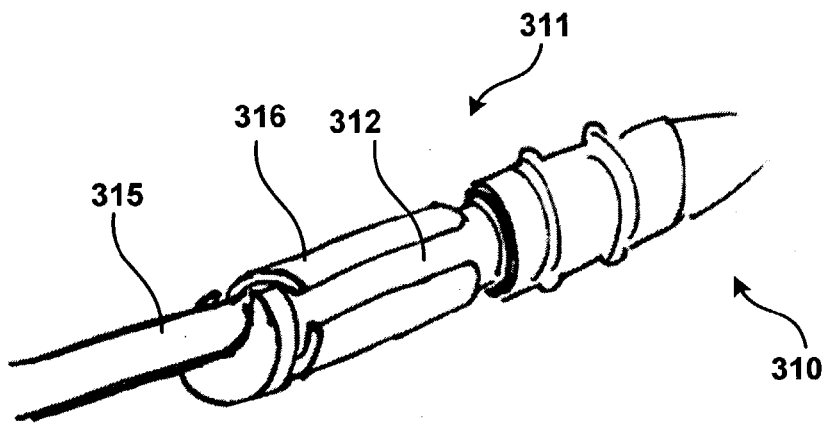
FIG. 32 is a perspective view of the extension illustrated in FIG. 30 following insertion of a lead and assembly of the extension.

FIG. 30 is another perspective view of a distal end 311 of a neurological lead extension 310. FIG. 31 is a cross-sectional view of distal end 311. FIG. 32 is a perspective view of a distal end 311 following insertion of lead 315 and assembly of extension 310. In this case, distal end 311 defines a channel 314 sized to receive a neurological lead 315. In particular, channel 314 may be formed in a receiving element 312 that includes the electrical contacts 313 for contacting an inserted lead. A sleeve 316 defines a slit 317 that is also sized to receive the neurological lead 315. Then, following insertion of lead 315 into channel 314 through the slit 317 of sleeve 316, sleeve 316 can be rotated relative to channel 314 to secure the inserted lead 315 within channel 314. The size of slit 317 may correspond to a diameter of a lead to be inserted, or larger, in order to ensure that the lead can be easily inserted into channel 314 though silt 317.

Figure 33:
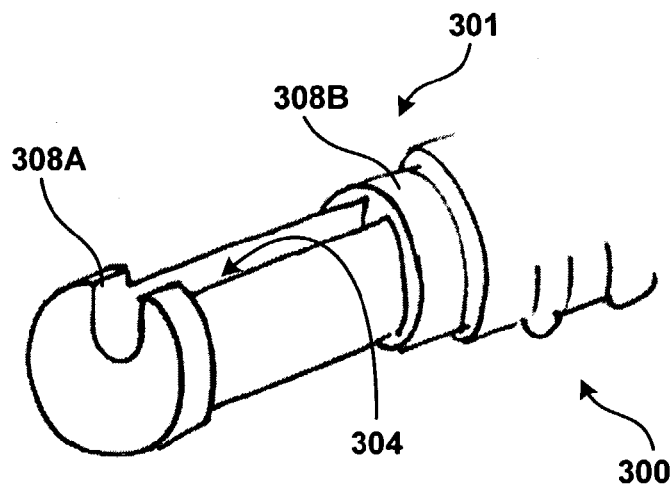
FIG. 33 is another perspective view of a distal end of a neurological lead extension having a feature to avoid shifting of a locking sleeve.

FIG. 33 is another perspective view of a distal end 301 of a neurological lead extension 300. In this case, distal end 301 defines a channel 304 sized to receive a neurological lead. Then, following insertion of the lead into channel 304, a sleeve (not shown) can be positioned over distal end 301. Distal end 301 may be formed with shoulders 308A, 308B to help ensure that the sleeve stays in place.

FIGS. 34–40 are perspective views illustrating assembly of a neurological lead into a neurological lead extension in accordance with an embodiment of the invention. The procedure is typically performed by a physician. As shown in FIG. 34, neurological lead 345 is inserted through an outer sheath 341, e.g., typically made of a silicone material. As shown in FIG. 35, neurological lead 345 is then inserted through a conduit of sleeve 342. As shown in FIG. 36, neurological lead 345 is positioned in a channel of bottom portion 354 of a distal end 351 of neurological lead extension 350. The proximal end of extension 350 is configured for attachment to a neurological device.

Top portion 352 is then assembled with bottom portion (as indicated by the arrow in FIG. 36), such that top portion 352 and bottom portion 354 define a bore that surrounds lead 345. FIG. 37 is a cross-sectional view illustrating such assembly to this point.

As shown in FIGS. 38 and 39, sleeve 342 is next positioned over top and bottom portions 352, 354 so as to secure lead within the bore formed by top and bottom portions 352, 354. Outer sheath 341 is then positioned over distal end 351 and tied down by sutures 359A and 359B to form a hermetic barrier as illustrated in FIG. 40. In this manner, simple assembly of a neurological lead 345 a neurological lead extension 350 can be performed without the need for set screws. Other embodiments described herein may be assembled in a similar manner consistent with the given embodiment.

Figure 41:
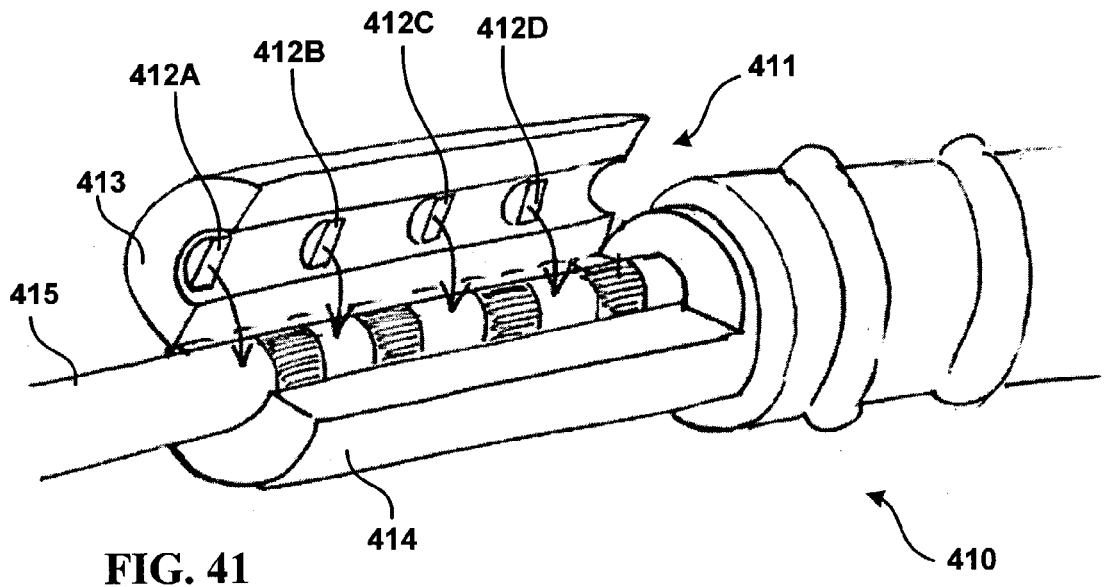
FIG. 41 is another perspective view of a distal end of a neurological lead extension.

FIG. 41 is another perspective view of a distal end 411 of a neurological lead extension 410. In this case, distal end 411 is formed with elements 412A–412D that mechanically interact with lead 415 following assembly, to secure the inserted end of lead 415 to the distal end 411. In particular, elements 412 may comprise a non-metallic material, e.g., molded as part of top portion 413 to protrude from top portion 413. Depressions in top portion could also be used, e.g., to engage with protrusions (not shown) on a lead or bottom portion 414. In any case, non-metallic elements 412 may ensure that lead 415 will hot dislodge from neurological lead extension 410 following assembly. Accordingly, the need for conventional set screws can be avoided.

Figure 42:
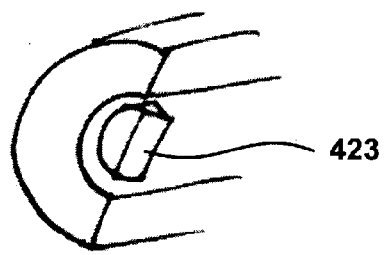
FIGS. 42–44 are perspective views illustrating elements that can be respectively formed in proximity to a distal end of a neurological lead extension to ensure that an inserted lead will not dislodge following assembly.
Figure 43:
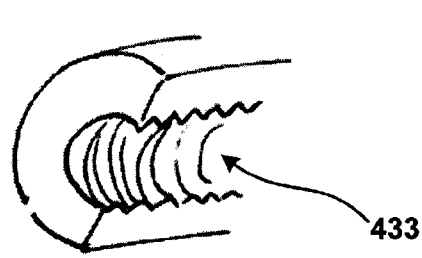
Figure 44:
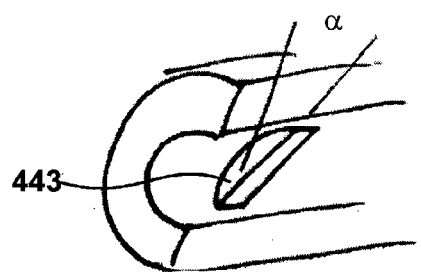

FIGS. 42–44 are perspective view illustrating elements that can be respectively formed in proximity to a distal end of a neurological lead extension to ensure that an inserted lead will not dislodge following assembly. A non-metallic protruding element 423 is illustrated in FIG. 42. A set of ridges 433, e.g., protrusions and depressions, are illustrated in FIG. 43. The non-metallic protruding element 443 illustrated in FIG. 44 may define an offset pitch, e.g., at angle α, corresponding to a similar depression of an inserted lead.

Figure 45:
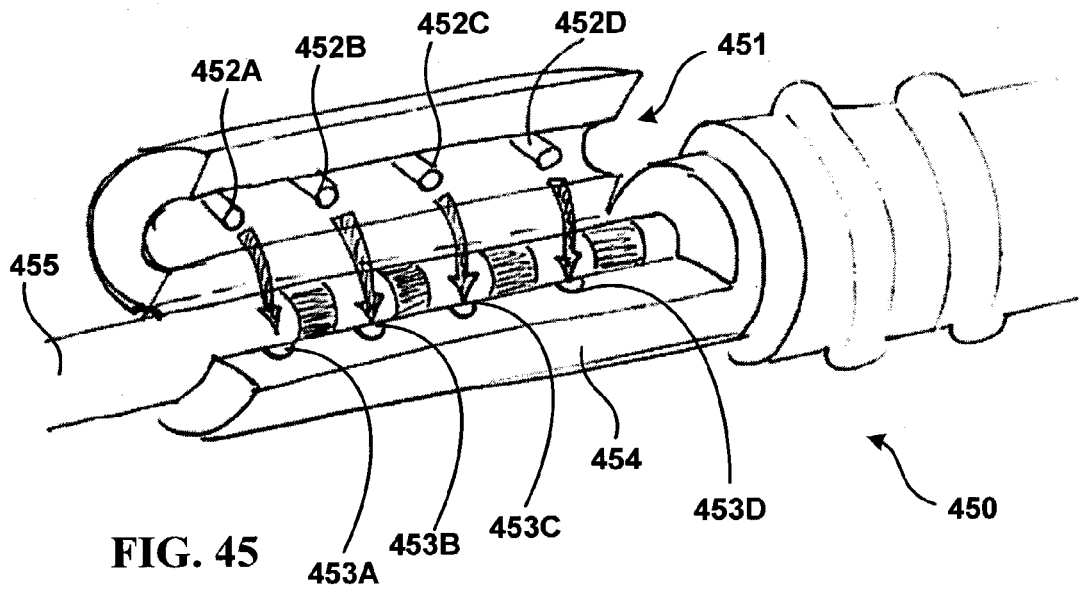
FIG. 45 is another perspective view of a distal end of a neurological lead extension with clamping against lead dislodgement by knobs pressing between lad connector rings.
Figure 46:
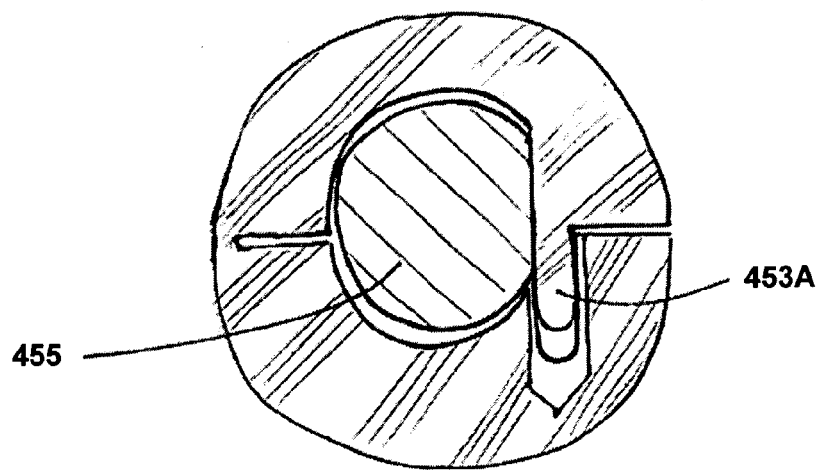
FIG. 46 is a cross-sectional side view of the extension illustrated in FIG. 45.

FIG. 45 is another perspective view of a distal end 451 of a neurological lead extension 450. FIG. 46 is a cross-sectional side view of distal end 451. In this case, distal end 451 is formed with elements 452A–452D that mechanically interact with lead 455 following assembly, to secure the inserted end of lead 455 to the distal end 451. In particular, elements 452 may comprise a non-metallic material, e.g., molded as part of top portion 453 to protrude from top portion 453. More specifically, elements 452 may comprise tangential pins that mate with holes 453A–453D of bottom portion 454. Such elements 452 may help ensure that lead 455 will not dislodge from neurological lead extension 450 following assembly. Lead 455 may be formed with grooves or depressions at locations associated with elements 452 following assembly. In this manner, conventional set screws can be eliminated.

Figure 47:
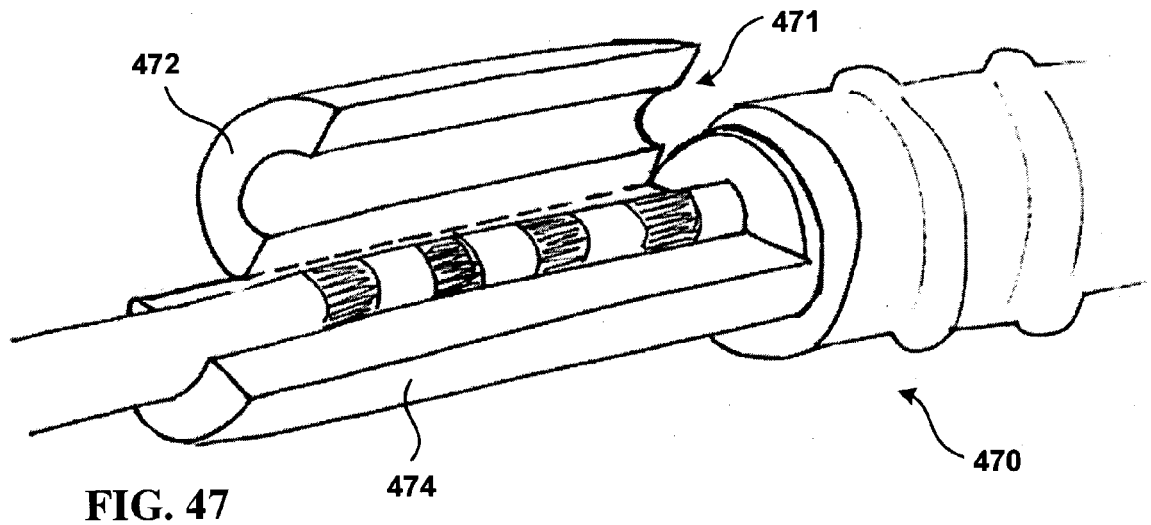
FIG. 47 is another perspective view of a distal end of a neurological lead extension.
Figure 48:
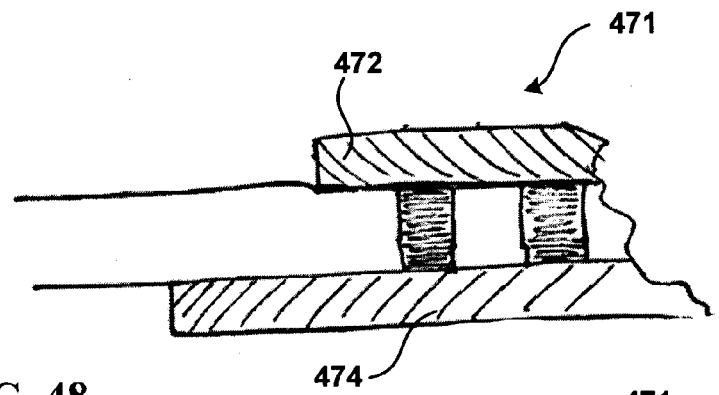
FIGS. 48 and 49 are alternative cross-sectional side views of the extension illustrated in FIG. 47.
Figure 49:
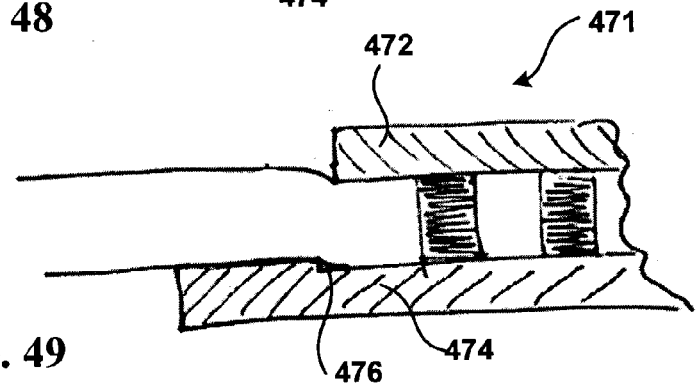

FIG. 47 is another perspective view of a distal end 471 of a neurological lead extension 470. FIGS. 48 and 49 are alternative cross-sectional side views of distal end 471. In this case, top portion 472 is notched such that it extends a shorter distance than bottom portion 474. As illustrated in FIG. 49, an element in the form of an edge 476 may be formed in bottom portion 474 such that after assembly, top portion 472 pushes lead over edge 476 to improve the retention force without the need for set screws.

Figures 50, 51:
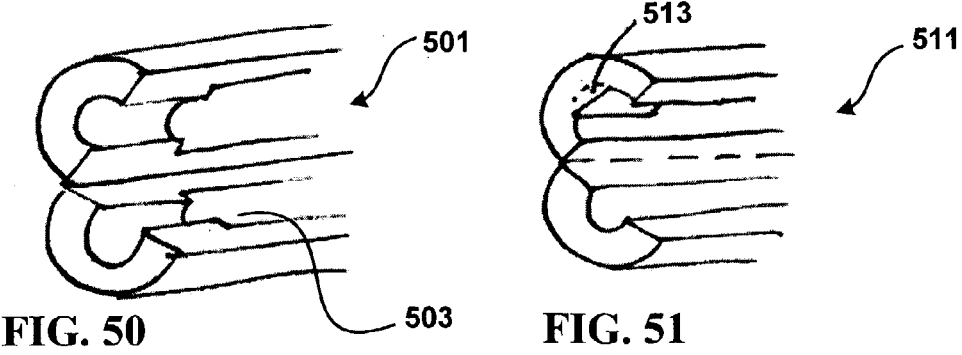
FIGS. 50 and 51 are additional perspective views of distal ends of exemplary neurological lead extensions.

FIGS. 50 and 51 are additional perspective views of distal ends 501, 511 of exemplary neurological lead extensions. As shown in FIG. 50, element 503 may define differential diameters of a bore formed by assembly of top and bottom portions 502, 504, e.g., to mechanically retain a lead having a similar differential diameter. Element 513 illustrated in FIG. 51 defines a flat plane that can increase retention force against an inserted lead to improve retention of an inserted lead.

Figure 52:
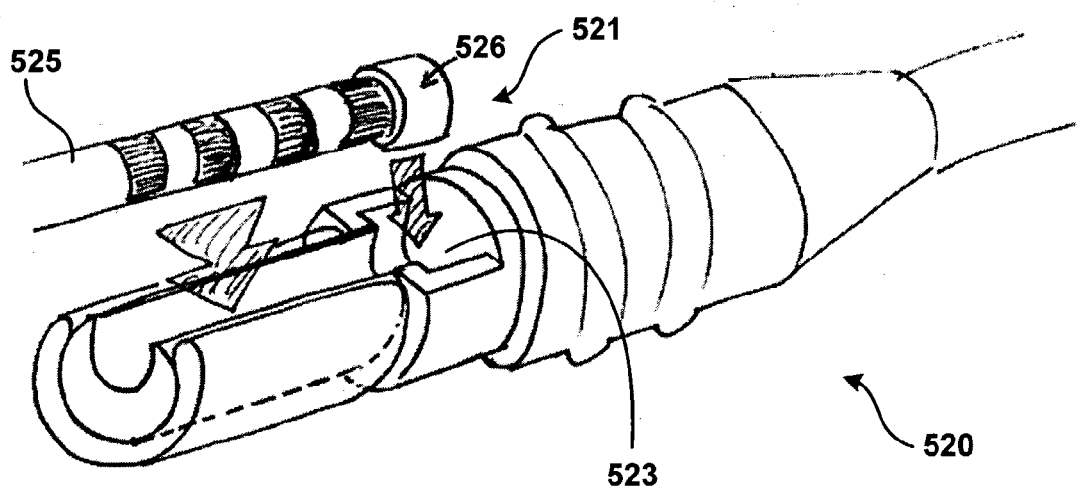
FIG. 52 is another perspective view of a distal end of a neurological lead extension.

FIG. 52 is another perspective view of a distal end 521 of a neurological lead extension 520. In this case, distal end 521 is formed with an element 523 in the form of a receiving area sized to receive an enlarged diameter portion 526 of lead 525.

Figure 53:
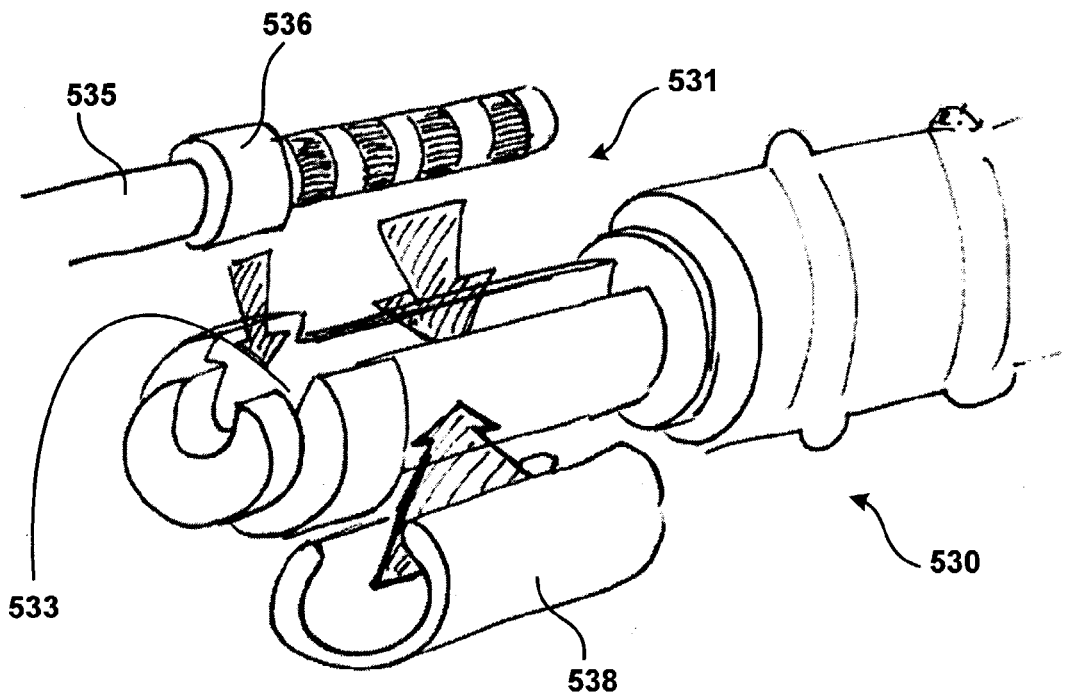
FIG. 53 is another perspective view of a distal end of a neurological lead extension with adjusted lead connector end to match a similarly designed lead extension.
Figure 54:
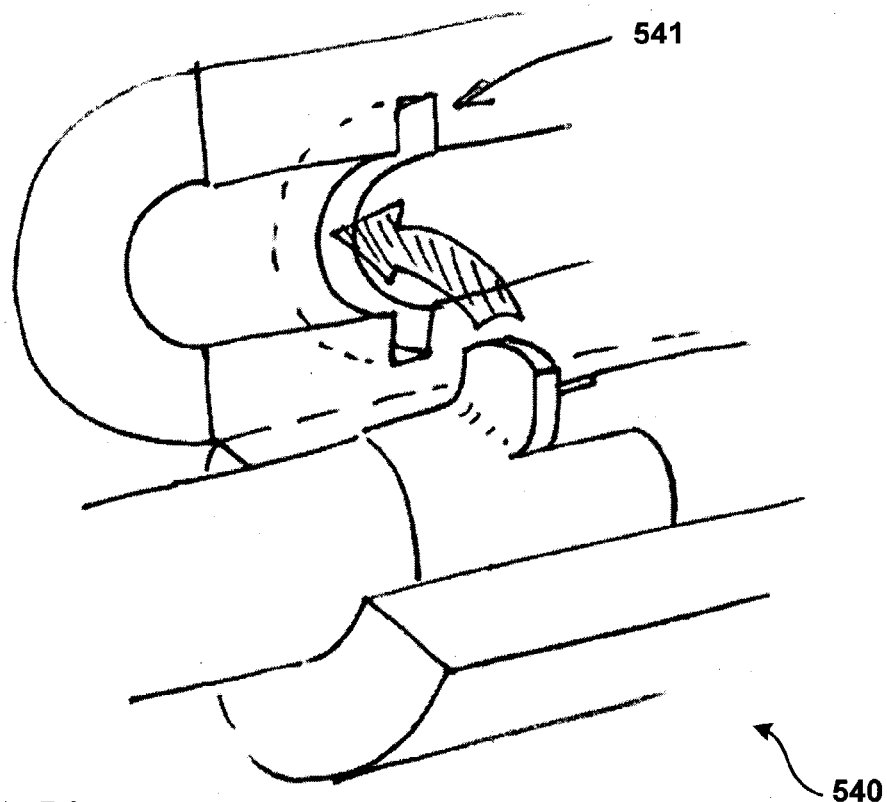
FIGS. 54–60 are perspective views respectively illustrating distal ends of neurological lead extensions receiving a neurological lead according to embodiments of the invention.
Figure 55:
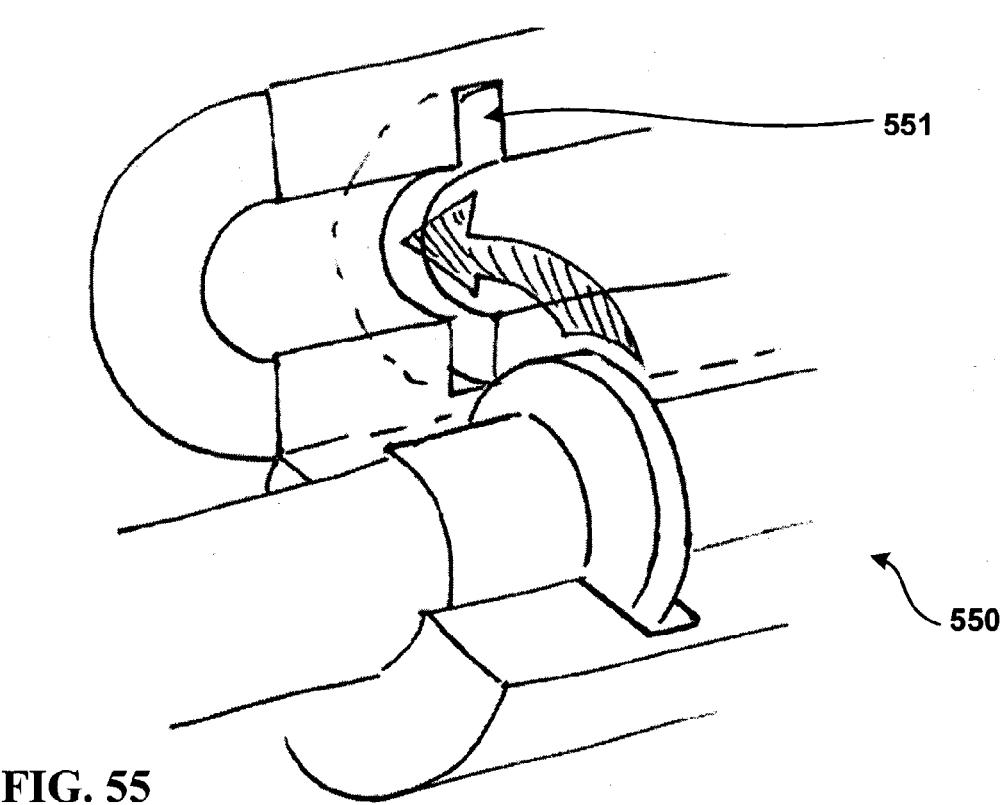
Figure 56:
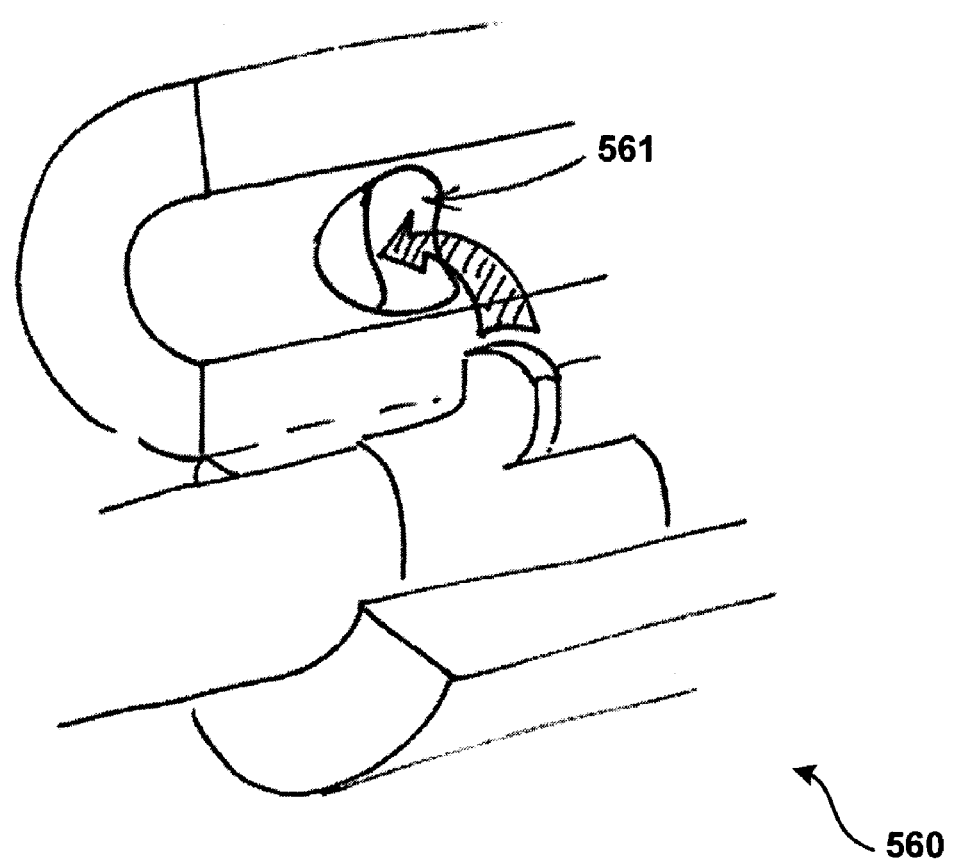
Figure 57:
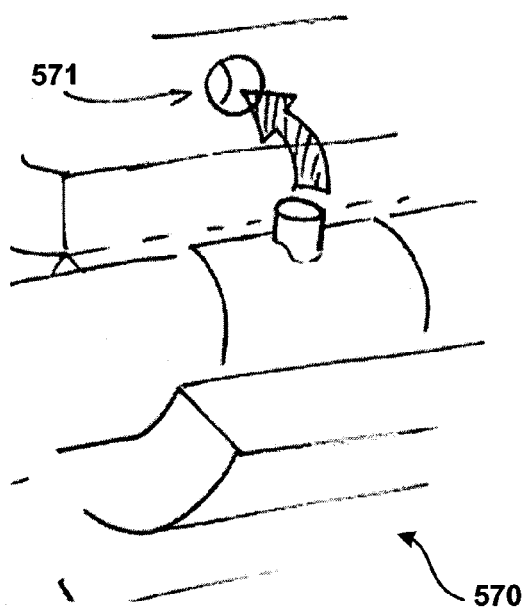
Figure 58:
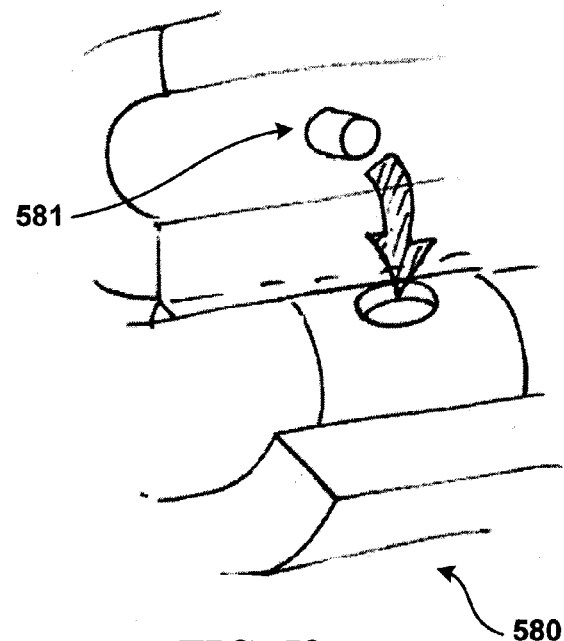
Figure 59:
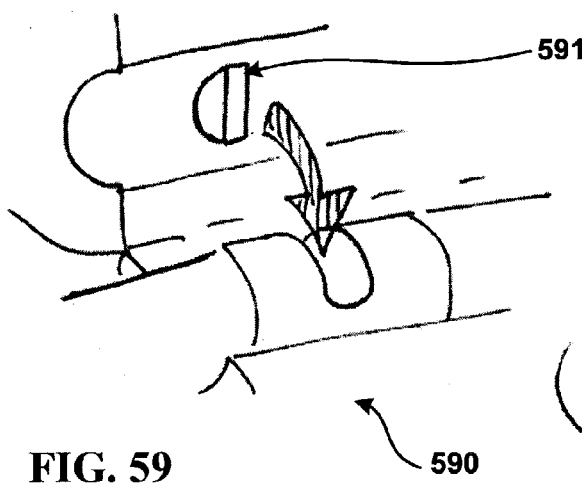
Figure 60:
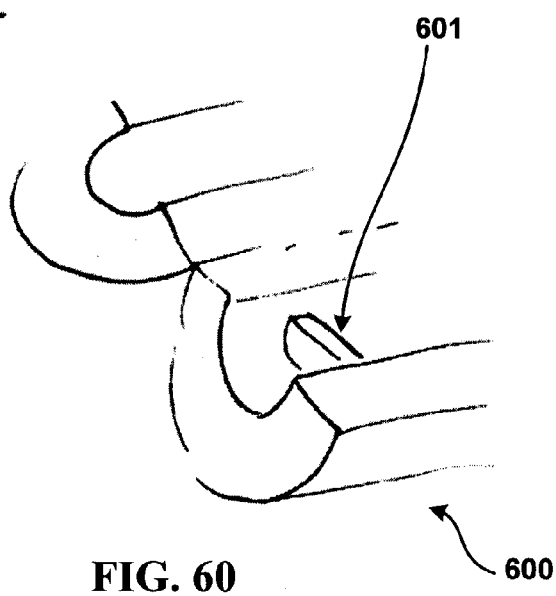

FIG. 53 is another perspective view of a distal end 531 of a neurological lead extension 530. Distal end 531 is formed with an element 533 in the form of a receiving area sized to receive an enlarged diameter portion 536 of lead 535. Sleeve 538 may also be used as outlined herein.

FIGS. 54–60 respectively illustrate distal ends of neurological lead extensions 540, 550, 560, 570, 580, 590, 600. In particular, FIGS. 54–60 illustrate various different elements 541, 551, 561, 571, 581, 591, 601 that may be formed in proximity to the respective distal end of the respective extension to improve retention of an inserted lead. Many other non-metallic elements could also be used so as to avoid the need for set screws, but ensure good retention of a lead within the extension.

A number of embodiments of the invention have been described. However, one skilled in the art will appreciate that the invention can be practiced with embodiments other than those disclosed. For example, one or more aspects of the invention may find use in other lead assemblies such as medical leads used for heart pacing, heart defibrillation, cardioversion, muscular simulation, and the like. The disclosed embodiments are presented for purposes of illustration and not limitation, and the invention is limited only by the claims that follow.

What is claimed is:

1. A medical lead extension comprising:
   a proximal end configured for attachment to a neurological device;
   a distal end formed to receive an implanted medical lead and electrically couple the implanted medical lead to the neurological device, wherein the distal end forms a laterally accessible channel sized to receive the implanted medical lead; and
   a set of electrical contacts disposed within the channel to electrically couple to corresponding electrical contacts disposed along a major axis of an inserted end of the implanted medical lead, wherein the laterally accessible channel allows the medical lead to be laterally placed in the channel such that the set of electrical contacts electrically couple to the corresponding electrical contacts disposed along a major axis of the inserted end of the medical lead when the medical lead is mechanically secured within the channel.

2. The medical lead of claim 1, further comprising a sleeve positioned over the distal end once the implanted medical lead is laterally placed in the channel such that the set of electrical contacts electrically couple to the corresponding electrical contacts disposed along the major axis of the inserted end of the medical lead, wherein the sleeve mechanically secures the implanted medical lead in the channel.

3. The medical lead extension of claim 2, wherein the sleeve includes a slit that corresponds to the channel and wherein the sleeve can be rotated to cover the channel once the implanted medical lead is laterally placed in the channel through the slit.

4. The medical lead extension of claim 2, wherein the sleeve is molded to define a conduit sized and shaped to correspond to a bottom portion of the distal end and the lead inserted within the channel.

5. The medical lead extension of claim 1, wherein the distal end comprises a top portion and a bottom portion, wherein the channel is formed in the bottom portion and the top and bottom portions assemble to form a bore around the medical lead once the medical lead is laterally placed in the channel.

6. The medical lead extension of claim 5, wherein the top portion and the bottom portion are hinged to one another such that the top portion moves relative to the bottom portion about an axis parallel to the channel.

7. The medical lead extension of claim 5, wherein one of the top and bottom portions includes a protruding element to mate with a hole formed in the other of the top and bottom portions.

8. The medical lead extension of claim 5, further comprising a sleeve positioned about the top and bottom portions following assembly of the top and bottom portions to form the bore around the medical lead.

9. The medical lead extension of claim 1, further comprising a depression formed in the channel and sized relative to a protrusion on the medical lead.

10. The medical lead extension of claim 1, further comprising a protrusion formed in the channel and sized to mate with a depression on the medical lead.

11. The medical lead extension of claim 1, wherein the medical lead extension comprises a neurological lead extension and the medical lead comprises a neurological lead.

12. The medical lead extension of claim 11, wherein the medical lead extension comprises a percutaneous neurological lead extension and the proximal end is configured for attachment to a cable that in turn attaches to an external neurological device.

13. The medical lead extension of claim 1, wherein the set of electrical contacts comprise wires molded into the distal end of the medical lead extension.

14. A medical lead assembly comprising:
   a neurological stimulation lead; and
   a lead extension for attachment to the neurological stimulation lead, the lead extension including:
      a proximal end configured for attachment to a neurological device;
      a distal end formed to receive the neurological stimulation lead and electrically couple the implanted medical lead to the neurological device, wherein the distal end forms a laterally accessible channel sized to receive the implanted medical lead; and
   a set of electrical contacts disposed within the channel to electrically couple to corresponding electrical contacts disposed along a major axis of an inserted end to contact an inserted end of the neurological stimulation lead, wherein the laterally accessible channel allows the medical lead to be laterally placed in the channel such that the set of electrical contacts electrically couple to the corresponding electrical contacts disposed along a major axis of the inserted end of the medical lead when the medical lead is mechanically secured within the channel.

15. The medical lead assembly of claim 14, further comprising a sleeve positioned over the distal end once the implanted medical lead is laterally placed in the channel such that the set of electrical contacts electrically couple to the corresponding electrical contacts disposed along the major axis of the inserted end of the medical lead, wherein the sleeve mechanically secures the implanted medical lead in the channel.

16. The medical lead assembly of claim 15, wherein the sleeve includes a slit that corresponds to the channel and wherein the sleeve can be rotated to cover the channel once the implanted medical lead is laterally placed in the channel through the slit.

17. The medical lead assembly of claim 15, wherein the sleeve is molded to define a conduit sized and shaped to correspond to a bottom portion of the distal end and the lead inserted within the channel.

18. The medical lead assembly of claim 14, wherein the distal end comprises a top portion and a bottom portion, wherein the channel is formed in the bottom portion and the top and bottom portions assemble to form a bore around the medical lead once the medical lead is laterally placed in the channel.

19. The medical lead assembly of claim 18, wherein the top portion and the bottom portion are hinged to one another such that the top portion moves relative to the bottom portion about an axis parallel to the channel.

20. The medical lead assembly of claim 18, wherein one of the top and bottom portions includes a protruding element to mate with a hole formed in the other of the top and bottom portions.

21. The medical lead assembly of claim 18, further comprising a sleeve positioned about the top and bottom portions following assembly of the top and bottom portions to form the bore around the medical lead.

22. The medical lead assembly of claim 14, further comprising a protrusion formed in the channel and sized to mate with a depression on the neurological stimulation lead.

23. The medical lead assembly of claim 14, wherein the lead extension comprises a percutaneous neurological lead extension.

24. The medical lead assembly of claim 14, wherein the set of electrical contacts comprise wires molded into the distal end of the lead extension.

25. A medical device comprising:
a neurological device;
a neurological stimulation lead; and
a lead extension for attaching the neurological stimulation lead to the neurological device, the lead extension including:
  a proximal end configured for attachment to the neurological stimulation device;
  a distal end formed to receive the neurological stimulation lead and electrically couple the implanted medical lead to the neurological device, wherein the distal end forms a laterally accessible channel sized to receive the implanted medical lead; and
a set of electrical contacts disposed within the channel to electrically couple to corresponding electrical contacts disposed along a major axis of an inserted end of the implanted medical lead, wherein the laterally accessible channel allows the medical lead to be laterally placed in the channel such that the set of electrical contacts electrically couple to the corresponding electrical contacts disposed along a major axis of the inserted end of the medical lead when the medical lead is mechanically secured within the channel.

26. The medical device of claim 25, further comprising a sleeve positioned over the distal end once the implanted medical lead is laterally placed in the channel such that the set of electrical contacts electrically couple to the corresponding electrical contacts disposed along the major axis of the inserted end of the medical lead, wherein the sleeve mechanically secures the implanted medical lead in the channel.

27. The medical device of claim 26, wherein the sleeve includes a slit that corresponds to the channel and wherein the sleeve can be rotated to cover the channel once the implanted medical lead is laterally placed in the channel through the slit.

28. The medical device of claim 26, wherein the sleeve is molded to define a conduit sized and shaped to correspond to a bottom portion of the distal end and the lead inserted within the channel.

29. The medical device of claim 25, wherein the distal end comprises a top portion and a bottom portion, wherein the channel is formed in the bottom portion and the top and bottom portions assemble to form a bore around the medical lead once the medical lead is laterally placed in the channel.

30. The medical device of claim 29, wherein the top portion and the bottom portion are hinged to one another such that the top portion moves relative to the bottom portion about an axis parallel to the channel.

31. The medical device of claim 29, wherein one of the top and bottom portions includes a protruding element to mate with a hole formed in the other of the top and bottom portions.

32. The medical device of claim 29, further comprising a sleeve positioned about the top and bottom portions following assembly of the top and bottom portions to form the bore around the medical lead.

33. The medical device of claim 25, further comprising a depression formed in the channel and sized to mate with a protrusion on the medical lead.

34. The medical device of claim 25, wherein the lead extension comprises a percutaneous lead extension.

35. The medical device of claim 25, wherein the set of electrical contacts comprise wires molded into the distal end of the medical lead extension.

* * * * *